United States Patent
Cheng et al.

(10) Patent No.: US 8,642,765 B2
(45) Date of Patent: Feb. 4, 2014

(54) AZAINDOLE-INDOLE COUPLED DERIVATIVES, PREPARATION METHODS AND USES THEREOF

(75) Inventors: Jingcai Cheng, Wuxi (CN); Qizheng Yao, Wuxi (CN); Zhaohui Wang, Wuxi (CN); Weiyi Hua, Wuxi (CN)

(73) Assignee: Jingcai Cheng, Wuxi, Jiangsu (CN)

( * ) Notice: Subject to any disclaimer, the term of this patent is extended or adjusted under 35 U.S.C. 154(b) by 336 days.

(21) Appl. No.: 12/663,461

(22) PCT Filed: Jun. 6, 2008

(86) PCT No.: PCT/CN2008/071228
§ 371 (c)(1),
(2), (4) Date: Jan. 6, 2010

(87) PCT Pub. No.: WO2008/151558
PCT Pub. Date: Dec. 18, 2008

(65) Prior Publication Data
US 2010/0137356 A1  Jun. 3, 2010

(30) Foreign Application Priority Data
Jun. 8, 2007 (CN) .......................... 2007 1 0023347

(51) Int. Cl.
*C07D 471/02* (2006.01)
*A01N 43/90* (2006.01)

(52) U.S. Cl.
USPC .......................................... 546/113; 514/300

(58) Field of Classification Search
USPC .......................................... 546/113; 514/300
See application file for complete search history.

(56) References Cited

U.S. PATENT DOCUMENTS 6,566,341 B1   5/2003   Wang et al.

FOREIGN PATENT DOCUMENTS

| CN | 1355789 A | 6/2002 |
|----|-----------|--------|
| CN | 1424312 A | 6/2003 |
| CN | 1720900 A | 1/2006 |
| CN | 1763005 A | 4/2006 |
| CN | 1840196 A | 10/2006 |

OTHER PUBLICATIONS

Kubinyi (3D QSAR in Drug Design: Ligand-Protein Interactions and Molecular Similarity, vol. 2-3, Springer, 1998, 800 pages. pp. 243-244 provided.*
Zhang et al. (Bioorganic & Medicinal Chemistry 16 (2008) 7127-7132).*
Wermuth, The Practice of Medicinal Chemsitry, 2d ed. (2003), 768 pages. Chapters 9-10 provided.*
Myoung Ju Moon et al., "Synthesis and structure-activity relationships of novel indirubin derivatives as potent antiproliferative agents with CDK2 inhibitory activities," Bioorganic & Medicinal Chemistry (2006), vol. 14, p. 237-246.
Lundberg, A.S. and Weinberg, R.A., "Control of the cell cycle and apoptosis," Eur J Cancer (1999) vol. 35, p. 531-539.
Sherr. C.J., "Cancer cell cycles," Science (1996) vol. 274, p. 1672-1677.
Keyomarsi. K. and Pardee, A.B., "Redundant cyclin overexpression and gene amplification in breast cancer cells," Proc Natl Acad Sci USA (1993), vol. 90, p. 1112-1116.
Gray, N. et al., "ATP-site directed inhibitors of cyclin-dependent kinases," Curr Med Chem (1999), vol. 6, p. 859-875.
deCarcer, G. et al., "Targeting cell cycle kinases for cancer therapy," Curr Med Chem (2007). vol. 14(9), p. 969-85.
Rudolph, J., "Inhibiting transient protein-protein interactions: lessons from the Cdc25 protein tyrosine phosphatases," Nat Rev Cancer (2007), vol. 7(3), p. 202-211.
Huwe, A., Mazitschek, R., and Giannis, A., "Small molecules as inhibitors of cyclin-dependent kinases," Angew Chem Int Ed (2003), vol. 42, p. 2122-2138.
Ji Xiujuan et al., Institute of Materia Medica, Chinese Academy of Medical Sciences, Modern Research on Chinese Medicinal Herbs, 1(1), 1995, p. 227-257, and English abstract.
Nam, S. et al. "Indirubin derivatives inhibit Stat3 signaling and induce apoptosis in human cancer cells," PNAS (2005), vol. 102(17), p. 5998-6003.
Roy, K.K. and Sausville, E.A., "Early development of cyclin dependent kinase modulators," Curr Pharm Design (2001), vol. 7(16), p. 1669-1687.
Doklady, Akad Nauk SSR, 1958, 118: 302-305.
Guyen, B. et al., "Synthesis and evaluation of analogues of 10H-indolo[3,2-b]-quinoline as G-quadruplex stabilizing ligands and potential inhibitors of the enzyme telomerase." Org. Biomol.Chem (2004), vol. 2, p. 981-988.
Wang, L.G, Ossowski, L., and Ferrari, A.C., "Androgen receptor level controlled by a suppressor complex lost in an androgen-independent prostate cancer cell line," Oncogene (2004), vol. 23, p. 5175-5184.
Knockaert, M. et al., "Independent actions on cyclin-dependent kinases and aryl hydrocarbon receptor mediate the antiproliferative effects of indirubins," Oncogene (2004), vol. 23, p. 4400-4412.
International Search Report of PCT/CN2008/071228, dated Sep. 4, 2008.

* cited by examiner

*Primary Examiner* — Robert Havlin
(74) *Attorney, Agent, or Firm* — Hamre, Schumann, Mueller & Larson, P.C.

(57) ABSTRACT

A novel class of azaindole-indole coupled derivatives, their preparation methods, pharmaceutical compositions containing the same and the uses thereof. The common structural feature of these derivatives is that they are coupled by azaindole and indole bi-molecule at different positions, forming extended pi-conjugated systems. Such derivatives inhibited cell growth and proliferation by various mechanisms. The present compounds have improved solubility, increased bioavailability, and thus have enhanced drug actions, and reduced medical dosages and undesired responses.

8 Claims, 1 Drawing Sheet

AZAINDOLE-INDOLE COUPLED DERIVATIVES, PREPARATION METHODS AND USES THEREOF

TECHNICAL FIELD

The present invention relates to a novel class of azaindole-indole coupled derivatives. The common structural feature of these derivatives is that they are coupled by azaindole and indole molecules at in different positions, forming extended pi conjugated heterocyclic systems. These derivatives inhibit cell growth and proliferation through various mechanisms. The invention also relates to the preparation methods of such derivatives, pharmaceutical compositions comprising the same and the uses thereof.

BACKGROUND

The present invention is the continuation application of "A specific indoles compounds and preparation methods thereof" (Application Number: 02138518.1; granted on May 4, 2005), "A pharmaceutical emulsion suitable for undissolved medicaments and preparation methods thereof" (Application Number: 200410052816.5; Application date: Jul. 14, 2007), "Preparation methods of N(1)-hydrocarbyl-3'-oximido indirubin derivatives (1) and medical uses thereof" (Application Number: 200510094482.2; granted on: Aug. 1, 2007) and "A dispersing agent suitable for undissolved medicaments" (Application Number: 200610038112.1; Application date: Jan. 17, 2006).

Monomeric compounds from plants are the major class among anti-tumor drugs. For instance, camptothecin isolated from *Camptothera acuminate* and paclitaxel obtained from *Cephalolaxus* are the well-known examples.

Through researching traditional medicinal plants with modern pharmaceutical methods, it is found that indirubin (1, indirubin, 2',3-bisindole, purple), a bisindole derivative contained in Qingdai, is effective in the treatment of chronic myelocytic leukemia (CML). It has advantages of quick onset, low dose, little side effects, and low cost, etc. Subsequently, extensive structural modifications and biological activity studies on bisindole compounds obtained from Qingdai [including indigo (2), 2,2'-bisindole, blue; isoindigo (3), 3,3'-bisindole, brown] were carried out. As a result, N-1-methylisoindigo was found to have better efficacy and lower toxicity than indirubin.

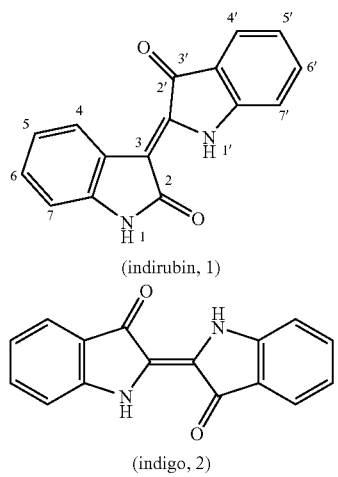

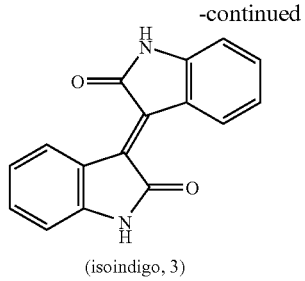
(isoindigo, 3)

Further studies demonstrate that the pharmacodynamic mechanism of indirubin and derivatives thereof inhibit tumor proliferation by inhibiting cyclin-dependent kinases (CDKs)

The cyclin-dependent kinases (CDKs) are typical serine (Ser)/threonine (Thr) kinases and signaling molecules of cell growth. CDKs mainly act on different phases of the cell cycle (a cell cycle is classified into four phases: $G_1$, S, $G_2$ and M), and allow for cell growth, proliferation (DNA replication and chromosome segregation), dormancy (cells are out of cell cycle and enter the quiescent period of cell division, known as the $G_0$ phase) or apoptosis. CDKs can also regulate nerve and thymus function. Unlike other kinases, a hybrid dimer complex formed with the corresponding cyclins is necessary for the catalytic functions of CDKs. At least 9 CDKs (CDK 1~9) and 11 cyclins (A~J) have been identified in human cells. Different CDKs bind to different cyclins or cyclin subunits. For instance, CDK1 (cdc2) binds to cyclin A and $B_1$-$B_3$; CDK2 binds to cyclin A, $D_1$-$D_3$ and E; CDK4, CDK5 and CDK6 bind to cyclin $D_1$-$D_3$; CDK5 also binds to pk35; CDK7 binds to cyclin H; and CDK6 binds to cyclin K which is D-related.

According to biomedicine research that have won 2001 Nobel Prize, "the relationship between proliferation and cancer", all kinds of abnormality of CDKs are present in almost all tumor cells[1-2], and cancer cells enter S, $G_2$ and M phases in cycles and immortalize. For example, over 85% of breast cancer patients demonstrate abnormality in cyclinE/CDK4/6[3]. Multiple tumors can be treated by inhibiting CDKs to effectively preventing cell proliferation (but not killing cells), thus, either promoting cell differentiation, or promoting cell apoptosis. It is believed that CDK inhibitors are a new class of anticancer drugs with broad spectrum. In addition, these drugs will have strong selectivity, good efficacy and low toxicity due to their cytostatic, not cytotoxic activity.

It is shown that CDK inhibitors effectively inhibit growth of various cancer cells, such as cancer of breast, colon, prostate, and brain tumor, etc. These compounds can also effectively inhibit clinically refractory androgen-independent prostate cancer cells (PC-3, DU-145), hormones and many other chemotherapy-resistant advanced metastatic prostate cancer cells due to their ability to inhibit cell proliferation, which is more significantly. As a result, it has become a new reasonable strategy to develop anticancer drugs by looking for CDK inhibitors[4-6].

So far, nearly 10 types of small molecule CDK inhibitors and/or regulating agents have been studied, which are mainly ATP-regional oriented CDK inhibitors[7]. Indirubin and N-1-methylisoindigo, which have been used clinically are one type of CDK inhibitors. In addition, UCN-01 and flavopiridol, which was developed by the National Cancer Institute (NCI) of United States, have entered clinical trails[10].

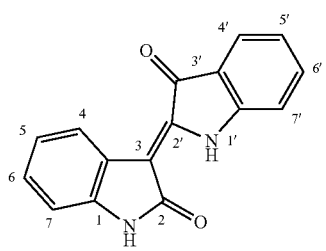

indirubin

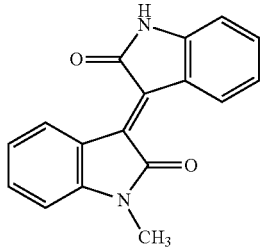

N-1-methylisoindigo

In summary, indirubin bisindole derivatives are important CDK inhibitors that have little toxic side-effects. However, clinical applications of these compounds are influenced by their poor water-solubility and liposolubility. In recent years, extensive structural modifications for indirubin derivatives have been made by many foreign pharmaceutical research institutions and pharmaceutical companies. However, the anti-tumor effects of indirubin bisindole derivatives are still dissatisfactory.

In a word, there's an urgent need to develop new CDK inhibitors with excellent performance.

SUMMARIZED OF THE INVENTION

The purpose of the present invention is to provide azaindole-indole coupled derivatives which can be used as CDK inhibitors. Such compounds have many advantages, such as high inhibitory activity, improved water solubility, etc.

Another purpose of the present invention is to provide preparation methods, pharmaceutical compositions and uses of the compounds.

In the first aspect of the present invention, azaindole-indole coupled derivatives having the formula (IG) or the pharmaceutically acceptable salts thereof are provided:

Y=Z    (IG)

wherein,

Y is an azaindole group represented by (Y1) or (Y2);

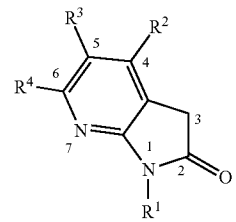

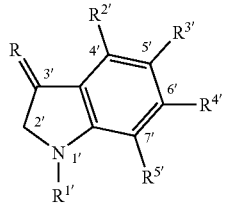

Z is an indole group represented by (Z1) or (Z2);

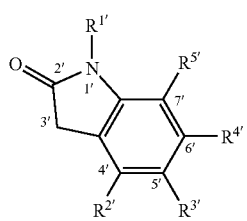

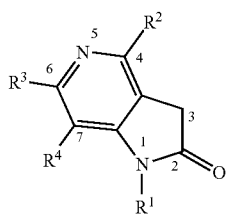

"=" represents double bond which is located between the 3-position of the azaindole group (Y) and the 2'- or 3'-position of the indole group (Z);

in the above Y1, Y2, Z1 and Z2, $R^1$ and $R^{1'}$ independently represent H or the following groups which may be unsubstituted or substituted by 1 to 3 substituents: $C_1$-$C_6$ alkyl, aryl, aralkyl, acyl, aroyl, glycosyl or biosyl protected by acyl, glycosyl or biosyl; wherein said substituents are selected from: halogen, hydroxyl, $C_1$-$C_3$ alkyl, nitro or amino;

$R^2$, $R^3$, $R^4$, $R^{2'}$, $R^{3'}$, $R^{4'}$ and $R^{5'}$ independently represent H, halogen, hydroxyl, sulfhydryl, or the following groups which may be unsubstituted or substituted by 1 to 3 substituents: $C_1$-$C_4$ alkyl, nitro, amino, amido, amide, $C_1$-$C_4$ alkoxy, methylthio, phenyl, phenoxy, aryl, aralkyl, trifluoromethyl, acyl, aroyl, sulfonic group, sulfamoyl, isocyanate, or alkyl isocyanate; wherein said substituents are selected from: halogen, hydroxyl, $C_1$-$C_3$ alkyl, nitro or amino.

R represents oxygen, sulfur, or selenium, or a $NR^6$ or $NOR^6$ group, wherein $R^6$ is H, or the following groups which may be unsubstituted or substituted by 1 to 3 substituents: $C_1$-$C_6$ straight-chain or branched-chain alkyl, aryl, aralkyl, $C_3$-$C_6$ alicyclic group, acyl, aroyl, sulfonyl or phosphoryl; wherein said substituents are selected from: halogen, hydroxyl, $C_1$-$C_3$ alkyl, nitro or amino.

In another preferred embodiment, the compounds are represented by (I), (II), (III) or (IV), wherein (I) is 5-azaindirubin derivatives, (II) is 5-azaisoindigo derivatives, (III) is 7-azaindirubin derivatives, and (IV) is 7-azaisoindigo derivatives:

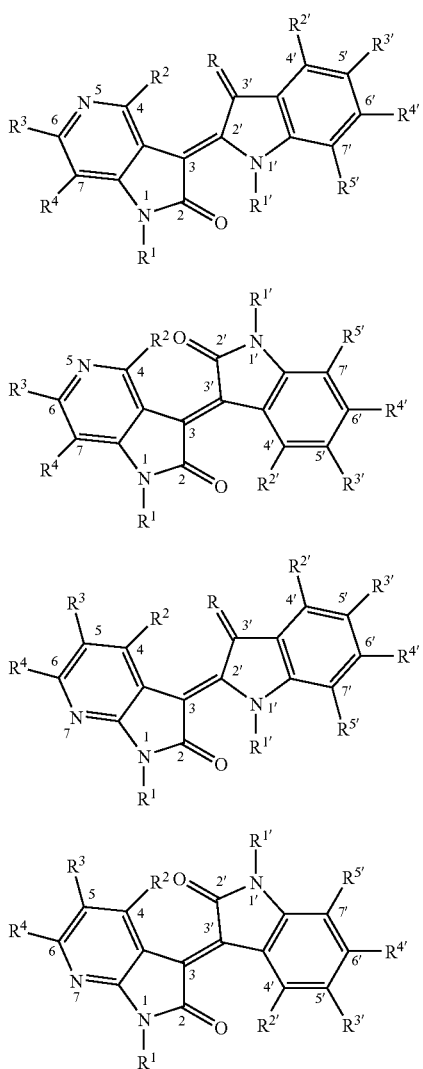

wherein, R, $R^1$, $R^2$, $R^3$, $R^4$, $R^{1'}$, $R^{2'}$, $R^{3'}$, $R^{4'}$ and $R^{5'}$ are defined as above.

In another preferred embodiment, $R^1$ and $R^{1'}$ independently represent H, $C_1$-$C_6$ alkyl, aryl, aralkyl, acyl, aroyl, glycosyl protected by acyl, or glycosyl;

$R^2$, $R^3$, $R^4$, $R^{2'}$, $R^{3'}$, $R^{4'}$ and $R^{5'}$ independently represent H, halogen, hydroxyl, sulfhydryl, $C_1$-$C_4$ alkyl, amino, amine, amide, $C_1$-$C_4$ alkoxy, methylthio, phenyl, phenoxy, aryl, aralkyl, trifluoromethyl, acyl, aroyl, sulfonic group, or isocyanate;

Glycosyl as mentioned above is arabinose, xylose, ribose, mannose, or glucose;

R represents oxygen, sulfur, or selenium, or a $NR^6$ or $NOR^6$ group, wherein $R^6$ is H, $C_1$-$C_6$ straight-chain or branched-chain alkyl, aryl, aralkyl, $C_3$-$C_6$ alicyclic group, acyl, aroyl, sulfonyl, or phosphoryl.

In another preferred embodiment, the compounds as described are selected from 5-azaindirubin derivatives (Table 1: compound Nos 1-59), 5-azaisoindigo derivatives (Table 2: compound Nos 60-89), 7-azaindirubin derivatives (Table 3: compound Nos 92-150), or 7-azaisoindigo derivatives (Table 4: compound Nos 151-180).

In another preferred embodiment, the pharmaceutically acceptable salts as described include salts derived from inorganic acids, such as hydrochloric acid, hydrobromic acid, phosphoric acid, nitric acid, and sulfuric acid, or organic acids, such as methanoic acid, acetic acid, propionic acid, succinic acid, naphthalene disulfonic acid (1, 5), asiatic acid, oxalic acid, tartaric acid, lactic acid, salicylic acid, benzoic acid, butylcarboxylic acid, diethylacetic acid, malonic acid, amber acid, fumaric acid, pimelic acid, hexanedioic acid, maleic acid, malic acid, aminosulfonic acid, phenylpropionic acid, gluconic acid, ascorbic acid, nicotinic acid, isonicotinic acid, ethanesulfonic acid, para-toluenesulfonic acid, citric acid and amino acid.

In the second aspect of the present invention, a pharmaceutical composition is provided comprising: (a) IG compounds of formula (IG) or the pharmaceutically acceptable salts thereof; and (b) pharmaceutically acceptable carriers.

In another preferred embodiment, the pharmaceutical composition further comprises other therapeutic agents (such as antineoplastic agents, dermatologic agents, drugs for immune system, drugs for nervous system, antidiabetic drugs).

In another preferred embodiment, that the dosage form of the pharmaceutical composition is low capacity injection, medium capacity injection, high capacity injection, powder injection, emulsion for injection, tablet, pill, capsule, paste, cream, patch, liniment, powder, spray, implantable agents, drop, suppository, ointment; various nano preparations, or liposomes which can be made into injections as described above.

In another preferred embodiment, the pharmaceutical composition as described can be used alone or in combination with other agents (such as surgery, one or more Western medicines, Chinese herbal medicines, radiotherapy, gene therapy, or biologic regulators).

In the third aspect of the present invention, a method for preparing the pharmaceutical composition is provided, comprising the following steps:

mixing (a) compounds of formula (IG) or the pharmaceutically acceptable salts thereof with (b) pharmaceutically acceptable carriers, thereby forming the pharmaceutical composition.

In the fourth aspect of the present invention, a use of compounds of formula (IG) or the pharmaceutically acceptable salts thereof in treating the following diseases is provided: diseases caused by abnormal cyclin-dependent kinases, disorders of cell growth and proliferation, or insulin resistance.

In another preferred embodiment, the diseases include malignant tumors, psoriasis, viral skin diseases, acquired immunodeficiency syndrome, nervous system diseases (such as neurodegenerative disorder and nervous disorder), and type 2 diabetes mellitus.

In the fifth aspect of the present invention, a composition is provided comprising the compounds of formula (IG) or the pharmaceutically acceptable salts thereof as cyclin-dependent kinase inhibitors.

In another preferred embodiment, the compositions as described are health care products (containing acceptable carriers for health care product), foods (containing bromatologically acceptable carriers) or cosmetic products (containing cosmetically acceptable carriers).

In the sixth aspect of the present invention, a method that can be used to inhibit mammalian cyclin-dependent kinases in vivo or in vitro, or to treat diseases caused by abnormal high activity of cyclin-dependent kinases is provided, comprising the following steps: administrating to a subject in need thereof the compounds of formula (IG) or the pharmaceutically acceptable salts thereof, or compositions containing compounds of formula (IG) or the pharmaceutically acceptable salts thereof.

In another preferred embodiment, the diseases caused by abnormal high activity of cyclin-dependent kinases are selected for the following group: malignant tumors, psoriasis, viral skin diseases, acquired immunodeficiency syndrome, and nervous system diseases (such as neurodegenerative disorder and nervous disorder).

DETAILED DESCRIPTION OF THE INVENTION

Figure 1:
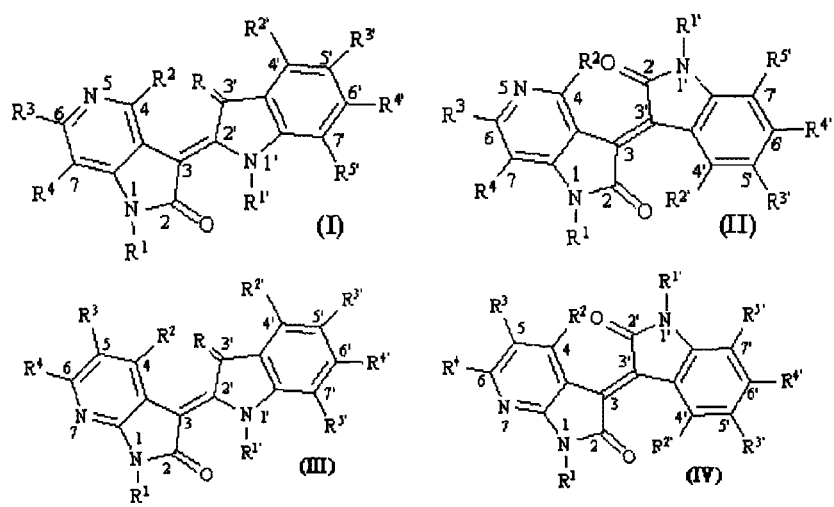
FIG. 1 shows the general formula of 5- or 7-azaindirubin derivatives and 5- or 7-azaisoindigo derivatives.

For the first time, the inventors develop a class of azaindole-indole coupled derivatives as CDK inhibitors. These compounds are formed by azaindole and indole molecules coupled at different positions, forming extended π conjugated heterocyclic systems. It has been indicated that this type of azaindole-indole coupled derivatives can produce biological activities through a variety of mechanisms, including inhibiting cell growth and proliferation, such as inhibiting cyclin-dependent kinases (CDKs), inducing endogenous cyclin-dependent inhibitors (CDKIs), and recovering insulin signal transformation, etc. As a result, these compounds can be used to treat various diseases caused by disorder of cell growth, including malignant tumors, psoriasis, viral skin diseases, acquired immunodeficiency syndrome, nervous system diseases (such as neurodegenerative disorder and nervous disorder), and type 2 diabetes mellitus caused by insulin resistance, etc.

Compounds of the Invention

As used herein, "compounds of the invention" or "azaindole-indole coupled derivatives of the invention" are used interchangeably. They both refer to compounds of formula (IG) or the pharmaceutically acceptable salts thereof.

Particularly, in the present invention, the structure of indirubin derivatives and isoindigo derivatives has been modified in order to improve solubility, increase bioavailability, enhance therapeutic effect, reduce drug dosage, and reduce untoward effects. Compared with the parental nucleus indirubin derivatives and isoindigo derivatives, compounds of the invention form extended π conjugated heterocyclic systems, thus improving the water solubility of the compounds.

Preferred compounds are represented by the general formula (I), (II), (III) or (IV), wherein (I) is 5-azaindirubin derivatives, (II) is 5-azaisoindigo derivatives, (III) is 7-azaindirubin derivatives, and (IV) is 7-azaisoindigo derivatives:

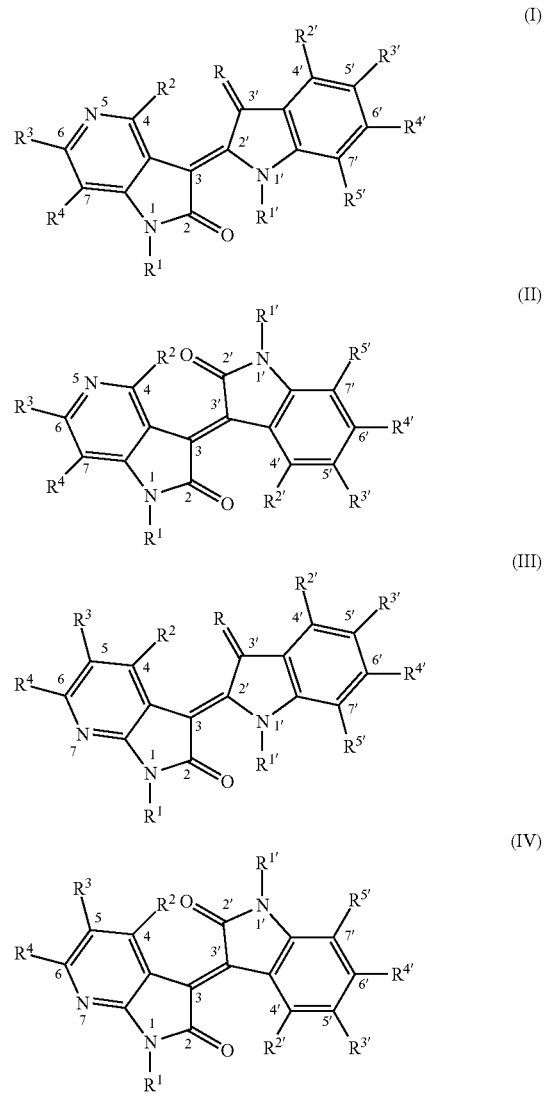

$R^1$ and $R^{1'}$ independently represent H or the following groups which may be unsubstituted or substituted by 1 to 3 substituents: $C_1$-$C_6$ alkyl, aryl, aralkyl, acyl, aroyl, glycosyl or biosyl protected by acyl, glycosyl or biosyl; wherein said substituents are selected from: halogen, hydroxyl, $C_1$-$C_3$ alkyl, nitro or amino;

$R^2$, $R^3$, $R^4$, $R^{2'}$, $R^{3'}$, $R^{4'}$ and $R^{5'}$ independently represent H, halogen, hydroxyl, sulfhydryl, or the following groups which may be unsubstituted or substituted by 1 to 3 substituents: $C_1$-$C_4$ alkyl, nitro, amino, amido, amide, $C_1$-$C_4$ alkoxy, methylthio, phenyl, phenoxy, aryl, aralkyl, trifluoromethyl, acyl, aroyl, sulfonic group, sulfamoyl, isocyanate, or alkyl isocyanate; wherein said substituents are selected from: halogen, hydroxyl, $C_1$-$C_3$ alkyl, nitro or amino.

R represents oxygen, sulfur, selenium; or a $NR^6$ or $NOR^6$ group, wherein $R^6$ is H, or the following groups which may be unsubstituted or substituted by 1 to 3 substituents: $C_1$-$C_6$ straight-chain or branched-chain alkyl, aryl, aralkyl, $C_3$-$C_6$ alicyclic group, acyl, aroyl, sulfonyl, or phosphoryl; wherein said substituents are selected from: halogen, hydroxyl, $C_1$-$C_3$ alkyl, nitro or amino.

Preferred compounds in the above compounds of general formula (I), (II), (III) and (IV) are:

wherein $R^1$ and $R^{1'}$ independently represent H, $C_1$-$C_6$ alkyl, aryl, aralkyl, acyl, aroyl, glycosyl protected by acyl, or glycosyl;

$R^2$, $R^3$, $R^4$, $R^{2'}$, $R^{3'}$, $R^{4'}$ and $R^{5'}$ independently represent H, halogen, hydroxyl, sulfhydryl, $C_1$-$C_4$ alkyl, amino, amidoamine, amide, $C_1$-$C_4$ alkoxy, methylthio, phenyl, phenoxy, aryl, aralkyl, trifluoromethyl, acyl, aroyl, sulfonic group, or isocyanate;

glycosyl as described above is arabinose, xylose, ribose, mannose, or glucose;

R represents oxygen, sulfur, selenium; or a $NR^6$ or $NOR^6$ group, wherein $R^6$ is H, $C_1$-$C_6$ straight-chain or branched-chain alkyl, aryl, aralkyl, $C_3$-$C_6$ alicyclic group, acyl, aroyl, sulfonyl, or phosphoryl.

The more preferred compounds are azaindole-indole coupled derivatives which are prepared in the examples (see the following table).

| Compound Nos | Categories |
|---|---|
| 1-59 | 5-azaindirubin derivatives |
| 60-89 | 5-azaisoindigo derivatives |
| 92-150 | 7-azaindirubin derivatives |
| 151-180 | 7-azaisoindigo derivatives |

Pharmaceutically Acceptable Salts

The present invention also includes salts formed by the invention compounds and pharmaceutically acceptable inorganic acids, such as hydrochloric acid, hydrobromic acid, phosphoric acid, nitric acid, sulfuric acid, or organic acids, such as methanoic acid, acetic acid, propionic acid, succinic acid, naphthalene disulfonic acid (1, 5), asiatic acid, oxalic acid, tartaric acid, lactic acid, salicylic acid, benzoic acid, butylcarboxylic acid, diethylacetic acid, malonic acid, amber acid, fumaric acid, pimelic acid, hexanedioic acid, maleic acid, malic acid, aminosulfonic acid, phenylpropionic acid, gluconic acid, ascorbic acid, nicotinic acid, isonicotinic acid, ethanesulfonic acid, para-toluenesulfonic acid, citric acid and amino acid.

Salts as described possess improved physicochemical property and enhanced cell permeability, and they can readily enter cells, thus improving the pharmacodynamic action.

Activities of the Compounds According to the Invention

The compounds according to the invention and salts thereof are cyclin-dependent kinase inhibitors, and can induce endogenous cyclin-dependent inhibitors (CDKIs), thus inhibiting cell growth and proliferation, and promoting apoptosis of tumor cells. The compounds and salts thereof sensitize the peripheral tissues to insulin, and reduce the insulin resistance by recovering insulin signal transformation. Therefore, compounds of the invention and salts thereof can be used as medicine to treat diseases caused by abnormal CDKs, disorders of cell growth and proliferation, and insulin resistance. The diseases include malignant tumors, psoriasis, viral skin diseases, acquired immunodeficiency syndrome, nervous system diseases (such as neurodegenerative disorder and nervous disorder), type 2 diabetes mellitus, etc.

For understanding the present invention, the inventors provide the following contents to describe the mechanism of the compounds according to the invention. However, it should be appreciated that the protection scope of the invention is not restricted by the mechanism as described.

In the present invention, azaindirubin derivatives are essentially the product from an azaindole molecule and an indole molecule coupled in the 3, 2'-position; while azaisoindigo derivatives are essentially the product from an azaindole molecule and an indole molecule coupled in the 3, 3'-position. A carbon atom within indole ring is replaced by a nitrogen atom, thereby obtaining the following four isomers:

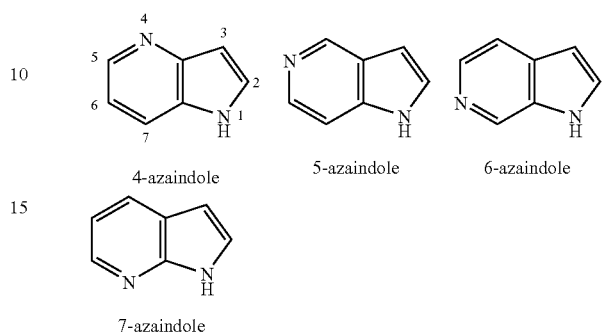

4-azaindole    5-azaindole    6-azaindole 7-azaindole

Purines (see the following figure) are one of ten CDK inhibitors, the chemical structure of which are currently known and which are the earliest studied CDK inhibitors[7]. With respect to the structure, azaindole and purines are very have many similar aspects, both of which are five-membered heterocycle fused to six-membered aromatic heterocycle.

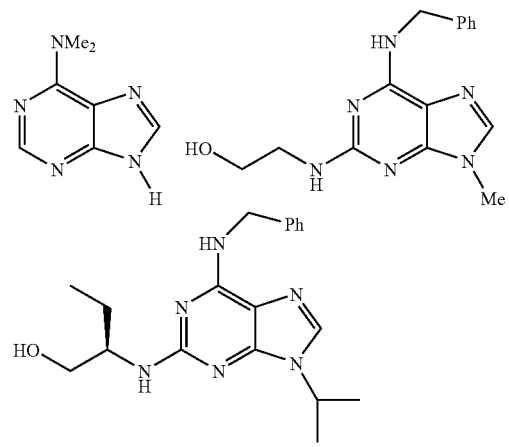

The results of the invention demonstrate that the compounds have similar activity as CDK inhibitors.

Non insulin dependent diabetes mellitus (type 2 diabetes mellitus) is one of the major diseases endangering human health and leading to death. The pathogenesis is insulin resistance. It has been demonstrated that indirubin derivatives have effect on the activity of PI3K (phosphatidylinositol-3-kinase) in the insulin signal transduction pathway. They can activate Akt (protein kinase) and inhibit mTOR (mammalian target of rapamycin), thus sensitizing the peripheral tissues to insulin, and reducing the insulin resistance.

Therefore, the derivatives of the invention can treat tumors, psoriasis, viral skin diseases, acquired immunodeficiency syndrome, nervous system diseases (such as neurodegenerative disorder and nervous disorder), and type 2 diabetes mellitus, etc.

Compositions and Administration Methods

The present invention also provides a composition containing the compounds according to the invention. Said composition can be used to inhibit the activity of CDKs, induce CDKIs, and recover insulin signal transformation. The compositions of the invention may be pharmaceutical compositions (containing pharmaceutically acceptable carriers), health care products (containing acceptable carriers for health care products), foods (containing bromatologically acceptable carriers) or cosmetic products (containing cosmetically acceptable carriers).

Preferably, compositions of the invention are pharmaceutical compositions, comprising the compounds of the invention (or the pharmaceutically acceptable salts thereof) as well as various pharmaceutically acceptable carriers or excipients.

The dosage form of pharmaceutical compositions according to the invention is not particularly limited, and it may be any clinically acceptable formulation. The dosage form of pharmaceutical compositions according to the invention includes: low capacity injection, medium capacity injection, high capacity injection, powder injection, emulsion for injection, tablet, pill, capsule, paste, cream, patch, liniment, powder, spray, implantable agents, drop, suppository, ointment; various nano preparations; and the corresponding liposomes which can be made into injection as mentioned above. Generally, pharmaceutical preparations should be compatible with the methods of administration.

Preferably, pharmaceutical compositions of the invention can be made into injection, liquid preparations, and solid dosage forms. The pharmaceutical composition, such as solid formulation, can be prepared by conventional methods. Preferably, pharmaceutical compositions, such as injection, liquid preparations, and solid formulation, should be made under sterile or appropriately decontaminated conditions.

In another preferred embodiments, the injections of compounds according to the invention (or the pharmaceutically acceptable salts thereof) are provided, that is, emulsion, submicron emulsion, nano-emulsion prepared using surfactants and/or solubilizers and/or oily components and/or other excipients.

In another preferred embodiments, solid dispersion preparations of compounds according to the invention (or the pharmaceutically acceptable salts thereof) are provided. The drugs are highly dispersed in inert carriers with water-solubility, water-insolubility, intestine-solubility, forming solid dispersion systems in the solid form, which in turn can be made into preparations, such as capsules, tablets, dropping pills, ointment, suppositories, injection and so on by conventional methods. Therefore, not only the highly dispersity of drugs can be maintained, but also the storage stability can be enhanced.

Administration Routes

When using the pharmaceutical composition, a safe and effective dose of compounds according to the invention is administered to mammals. Said dose is usually at least 1 µg/day, and in most cases no more than about 10 mg/kg of body weight. Preferably, the dose is between about 1 µg and about 3 mg per kilogram of body weight per day. Of course, with respect to the specific dose, factors, such as administration routes, health status of patients, should be taken into consideration, which are within the capability of an experienced physician.

The invention compounds (or the pharmaceutically acceptable salts) can be used alone or in combination with other drugs.

Preferred combination includes: in combination with surgery, in combination with one or more Western medicines, in combination with Chinese herbal medicines, in combination with radiotherapy, in combination with gene therapy, or in combination with biologic regulators.

The administration routes of the pharmaceutical compositions according to the invention is not particularly limited, including but not limit to: oral administration, injection, intratumor administration, embedding administration, intracavitary administration, rectal administration, transdermal delivery, internal and external application.

Preferred injection includes: intravenous injection, intramuscular injection, subcutaneous injection, and intracavity injection.

Preparation Methods

The compounds according to the invention of general formula (IG) can be prepared by the following procedure and known synthetic methods in the art. Generally, during the preparation procedure, the reactions are performed between −10° C. and reflux temperature, usually between room temperature (about 25° C.) and reflux temperature. Preferably, the reaction temperature is between 5° C. and 100° C., more preferably, between 20° C. and 80° C. Reaction time is not particularly limited. Generally, the reaction time is between 1 minute and 24 hours, preferably, between 1 hour and 20 hours. The solvents are usually polar solvents, such as water, DMF, alcohol (such as methanol, ethanol, and isopropanol, etc.). The structures of synthesized compounds can be identified by physico-chemical methods, such as hydrogen spectrum ($^1$H-NMR), mass spectrometry (MS) and elemental analysis.

1. Intermediates and target compounds of 5-azaindirubin (General Formula I)

(1) Synthesis of the intermediates:
1-hydrocarbyl-5-azaindole-2,3-dione (A):

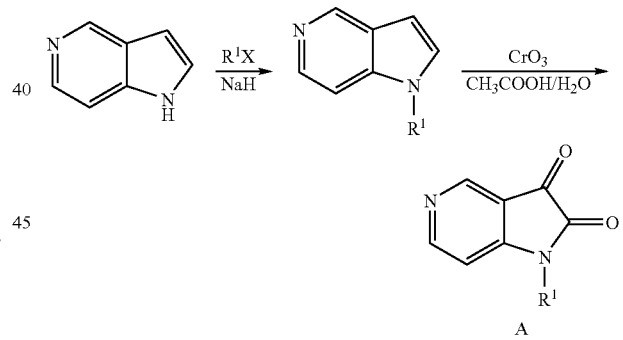

wherein, $R^1$ represents $CH_3$, $C_2H_5$, n-$C_3H_7$, n-$C_4H_9$, Ph-$CH_2$, glycosyl protected by acyl and so on.

1-hydrocarbyl-5-azaindole-2,3-dione (A) was prepared from 5-azaindole by hyarocarbylation at N–1 position, and then oxidation with $CrO_3$ and $CH_3COOH^{[11]}$.

(2) Synthesis of the intermediates:
1-acetyl-3-hydroxyindole derivatives (B)

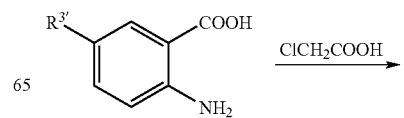

-continued

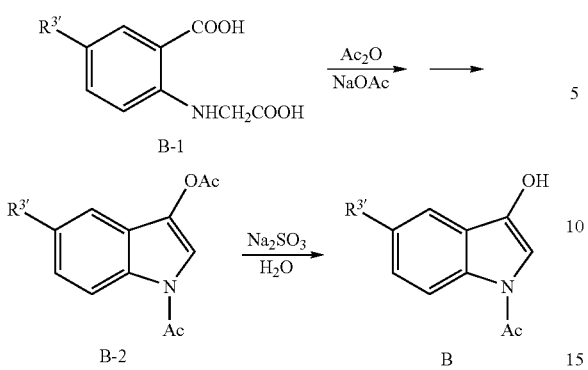

wherein, R³' represents H, Cl, Br, F, CH₃, OCH₃, SCH₃, Ph and so on.

The product B was prepared from 2-amino-benzoic acid derivatives by substitution with chloroacetic acid, acylation and cyclization in the presence of acetic anhydride and sodium acetate, and reduction.

(3) Synthesis of the target compounds:
5-azaindirubin derivatives (I)

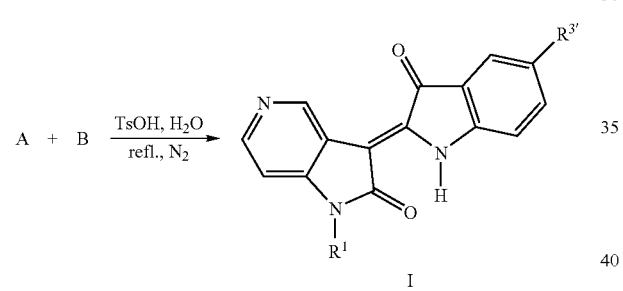

wherein, R¹ represents CH₃, C₂H₅, n-C₃H₇, n-C₄H₉, Ph-CH₂, glycosyl protected by acyl and so on; R³' represents H, Cl, Br, F, CH₃, OCH₃, SCH₃, Ph and so on.

1-hydrocarbyl-5-azaindole-2,3-dione and 1-acetyl-3-hydroxyindole or 5-halogen substituted-1-acetyl-3-hydroxyindole were heated at reflux respectively under N₂ in acidic condition, forming 1-hydrocarbyl-5-azaindirubin derivatives (I).

(4) Synthesis of the target compounds: 3'-oximido-5-azaindirubin derivatives

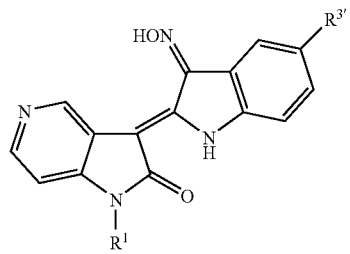

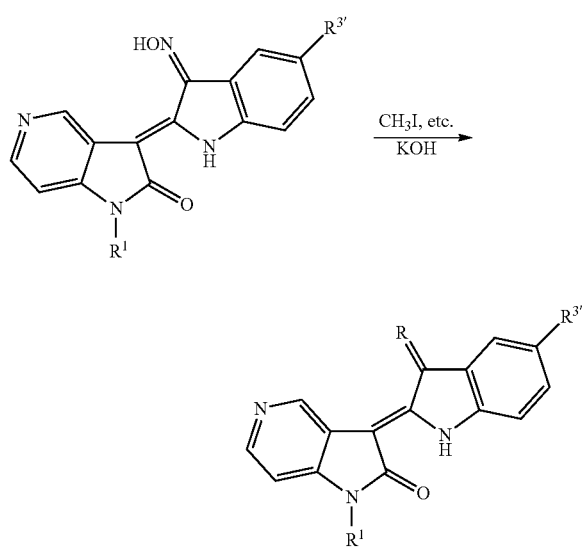

wherein, R¹ represents CH₃, C₂H₅, n-C₃H₇, n-C₄H₉, Ph-CH₂, glycosyl protected by acyl and so on, R³' represents H, Cl, Br, F, CH₃, OCH₃, SCH₃, Ph and so on.

(5) Synthesis of the target compounds:
5-azaindirubin-3'-oxime ether, etc.

Wherein, R represents CH₃ON, C₂H₅ON, R¹ represents CH₃, C₂H₅, n-C₃H₇, n-C₄H₉, Ph-CH₂ and so on, R³' represents H, Cl, Br, F and so on.

2. Target compounds of 5-azaisoindigo

General Formula II

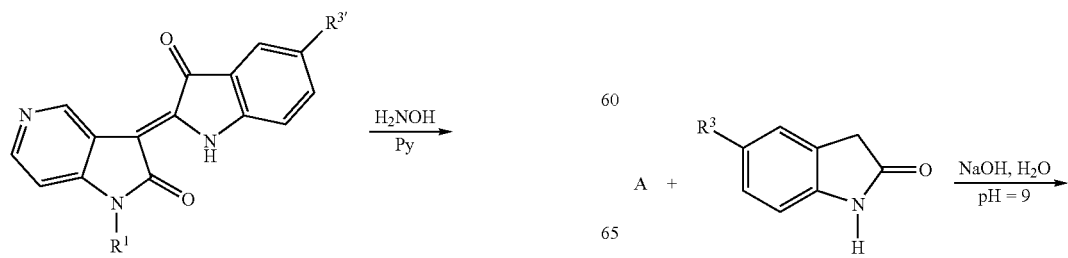

-continued

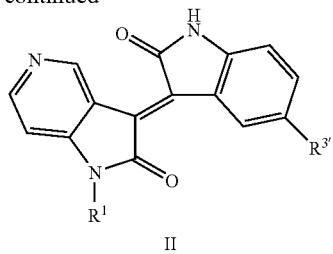

wherein, $R^1$ represents $CH_3$, $C_2H_5$, n-$C_3H_7$, n-$C_4H_9$, Ph-$CH_2$, glycosyl protected by acyl and so on, $R^{3'}$ represents H, Cl, Br, F, OH, $OCH_3$ and so on.

1-hydrocarbyl-5'-substitution-5-azaisoindigo derivatives (II) are prepared by reacting 1-hydrocarbyl-5-azaindole-2,3-dione (A) with 5-substituted-2-hydroxyindole in alkaline condition.

3. Intermediates and target compounds of 7-azaindirubin

General Formula III (1) Synthesis of the intermediates:
1-hydrocarbyl-7-azaindole-2,3-dione (C)

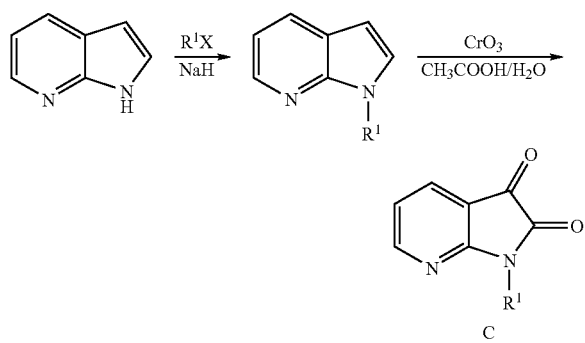

wherein, $R^1$ represents $CH_3$, $C_2H_5$, n-$C_3H_7$, n-$C_4H_9$, Ph-$CH_2$, glycosyl protected by acyl and so on.

1-hydrocarbyl-7-azaindole-2,3-dione (C) was prepared from 7-azaindole by alkylation at N–1 position, and then oxidation with $CrO_3$ and $CH_3COOH$[11].

(2) Synthesis of the target compounds: 7-azaindirubin (III)

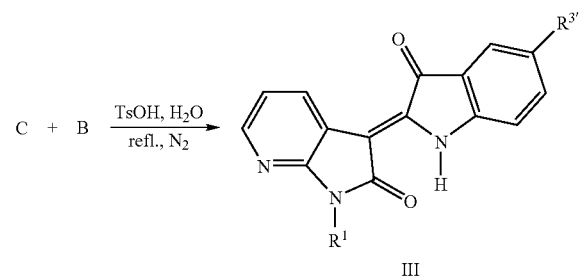

wherein, $R^1$ represents $CH_3$, $C_2H_5$, n-$C_3H_7$, n-$C_4H_9$, Ph-$CH_2$, glycosyl protected by acyl and so on, $R^{3'}$ represents H, Cl, Br, F, $CH_3$, $OCH_3$, $SCH_3$, Ph and so on.

1-hydrocarbyl-7-azaindole-2,3-dione and 1-acetyl-3-hydroxyindole or 5-halogen substituted-1-acetyl-3-hydroxyindole were heated at reflux respectively under $N_2$ in acidic condition, forming 1-hydrocarbyl-7-azaindirubin derivatives (III).

(3) Synthesis of the target compounds:
3'-oximido-7-azaindirubin

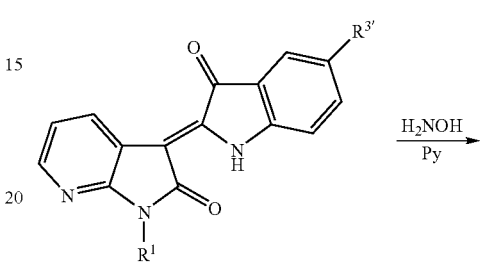

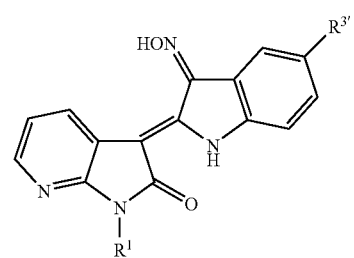

wherein, $R^1$ represents $CH_3$, $C_2H_5$, n-$C_3H_7$, n-$C_4H_9$, Ph-$CH_2$, glycosyl protected by acyl and so on, $R^{3'}$ represents H, Cl, Br, F, $CH_3$, $OCH_3$, $SCH_3$, Ph and so on.

(4) Synthesis of the target compounds:
7-azaindirubin-3'-oxime ether, etc.

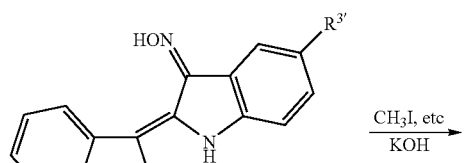

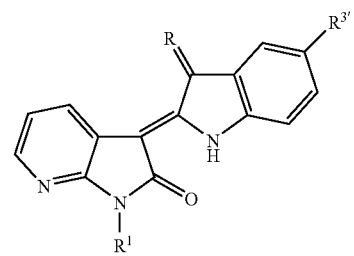

wherein, R represents $CH_3ON$, $C_2H_5ON$, $R^1$ represents $CH_3$, $C_2H_5$, n-$C_3H_7$, n-$C_4H_9$, Ph-$CH_2$ and so on, $R^{3'}$ represents H, Cl, Br, F and so on.

4. Target compounds of 7-azaisoindigo (Formula IV)

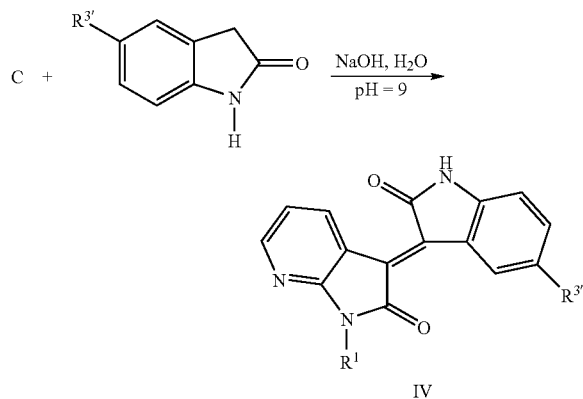

wherein, $R^1$ represents $CH_3$, $C_2H_5$, n-$C_3H_7$, n-$C_4H_9$, Ph-$CH_2$, glycosyl protected by acyl and so on, $R^{3'}$ represents H, Cl, Br, F, OH, $OCH_3$ and so on.

1-hydrocarbyl-5'-substitution-7-azaisoindigo derivatives (IV) were prepared by reacting 1-hydrocarbyl-7-azaindole-2,3-dione (C) with 5-substituted-2-hydroxy-indole in alkaline condition.

The main advantages of the invention are:

(1) The present invention has completely changed atomic composition of the parental nucleus of indirubin and isoindigo, thus forming a class of compounds with new structures, and improving the electrical properties of the original molecules. Based on the property that pyridine is soluble in water and benzene is almost insoluble in water, the water solubility of the compounds of the present invention has been improved, thus increasing the bioavailability.

(2) The compounds according to the invention, belonging to cyclin-dependent kinase inhibitors, can induce endogenous cyclin-dependent inhibitors, which in turn inhibit cell growth and proliferation, and promote apoptosis of tumor cells.

(3) The compounds according to the invention can sensitize the peripheral tissues to insulin, and reduce insulin resistance through recovering insulin signal transformation.

(4) The compounds according to the invention possess improved physicochemical property and enhanced cell permeability, and they can readily enter cells, thus improving the pharmacodynamic action.

EXAMPLES

The present invention is further illustrated through the following examples. It should be appreciated that the following examples are provided merely for the purposes of illustration and not intended to limit the scope of the invention. In examples, the experimental methods usually follow conventional methods, or recommendations from manufacturers, unless particularly indicated. Unless otherwise indicated, the portion and percentage are mass portion and weight percentage.

Example 1

Preparation of the Compounds

The melting points of 5- or 7-azaindirubin derivatives and 5- or 7-azaisoindigo derivatives, which were prepared in this example, were measured by Mel-TEMP melting point instrument without calibration. The mass spectrum (MS) was determined using HP1100LC/MSD mass spectrometer. The thin layer chromatographic (TLC) plates were made from silica gel $GF_{254}$ (Qingdao Haiyang Chemical Co., Ltd) and 0.8% CMC-Na solution in distilled water, activated at 100-110° C. for 1 hour, preserved in the dryers, and developed under ultraviolet light (at 254 nm and 365 nm). The chromatographic columns were packed with silica gel (200-300 mesh or 100-200 mesh) (Qingdao Haiyang Chemical Co., Ltd) employing dry method. The hydrogen spectrum (1H-NMR) was determined using Bruck AV-300 nuclear magnetic resonance apparatus with TMS as an internal standard. The elemental analysis was performed using Elementar Vario EL III apparatus.

The reagents were commercially available chemically pure and analytically pure grade products. Unless otherwise indicated, the reagents were used directly without any treatments.

Example 1-1

Preparation of the Intermediates (1) 1-methyl-5-azaindole-2,3-dione

To a solution of 1-methyl-5-azaindole (2.0 g, 15 mmol) in 70 ml acetic acid, a suspension of 3.2 g of $CrO_3$ in 20 ml water was added. The reaction mixture was stirred for 0.5 h at room temperature, and diluted by water. The mixture was extracted by trichloromethane for three times, the combined organic phases were washed with water, dried and evaporated. An orange intermediate (1-methyl-5-azaindole-2,3-dione) (1.5 g, yield: 62%; mp: 140-142° C.) was obtained.

(2) 2-(N-carboxymethylamino)-5-chlorobenzoic acid

To a solution of 2-amino-5-chlorobenzoic acid (2.0 g, 11.6 mmol) in 15 ml of 2 N $Na_2CO_3$, a solution of chloroacetic acid (0.69 g, 7.3 mmol) in 7.5 ml of 2 N $Na_2CO_3$ was added dropwise. After stirred for 20 hours at 80° C., the reaction mixture was cooled down to room temperature. 50 ml ether and 8 ml of 2 N hydrochloric acid were added to the mixture. The organic phase was separated, and dried with $MgSO_4$. After concentration, a light brown solid was obtained. A white solid (2-(N-carboxymethylamino)-5-chlorobenzoic acid) (1.58 g, yield: 59%; mp: 182-183° C.) was obtained through silica gel column chromatography (ethyl acetate/methanol, v/v, 1/1).

(3) 1-acetyl-5-chloro-3-acetoxyindole 2-(N-carboxymethylamino)-5-chlorobenzoic acid (1.20 g, 5.2 mmol) and anhydrous sodium acetate (0.6 g, 7.3 mmol) were dissolved in 8 ml acetic anhydride. After stirred for 5 hours at 60° C., the reaction mixture was cooled down to room temperature, and the sodium acetate was filtered off. The filtrate was concentrated, and the residue was dissolved in 100 ml ethyl acetate. 100 ml water and 20 ml saturated sodium bicarbonate were added to the solution, and the organic layer was separated. The aqueous layer was extracted with ethyl acetate (50 ml×2). The combined organic phases were washed with saturated sodium bicarbonate (100 ml×2), dried, and evaporated, to obtain a white solid (1-acetyl-5-chloro-3-acetoxyindole) (0.84 g, yield: 64%).

(4) 1-acetyl-5-chloro-3-hydroxyindole 1-acetyl-5-chloro-3-acetoxyindole (1.0 g, 3.97 mmol) and sodium sulfite (1.0 g, 7.94 mmol) were mixed in 20 ml water. After heated for 3 hours at 80° C., the reaction mixture was cooled down to room temperature, and then extracted with ethyl acetate (50 ml×2). The combined organic phases were dried and evaporated to obtain a solid as white needles (1-acetyl-5-chloro-3-hydroxyindole) (0.55 g, yield: 66%; mp: 186-188° C.).

(5) 1-methyl-7-azaindole-2,3-dione

To a solution of 1-methyl-7-azaindole (2.0 g, 15 mmol) in 70 ml acetic acid, a suspension of 3.2 g of $CrO_3$ in 20 ml water was added. The reaction mixture was stirred for 0.5 h at room temperature, and diluted by water. The mixture was extracted with trichloromethane for three times. The combined organic phases were washed with water, dried and evaporated. An orange intermediate (1-methyl-7-azaindole-2,3-dione) (1.73 g, yield: 71.3%; mp: 162-163° C.) was obtained.

(6) 2-(N-carboxymethylamino)-5-bromobenzoic acid

To a solution of 2-amino-5-bromobenzoic acid (2 g, 9 mmol) in 15 ml of 2 N $Na_2CO_3$, a solution of chloroacetic acid (0.69 g, 7.3 mmol) in 7.5 ml of 2 N $Na_2CO_3$ was slowly added dropwise. Then, after stirred for 20 hours at 80° C., the reaction mixture was cooled down to room temperature. 50 ml of ether and 8 ml of 2 N hydrochloric acid were added to the mixture. The organic phase was separated, and dried with $MgSO_4$. After evaporation, a light brown solid was obtained. The solid was purified by silica gel column chromatography (ethyl acetate/methanol, v/v, 1/1) to obtain a white solid (2-(N-carboxymethylamino)-5-bromobenzoic acid) (1.55 g, yield: 60%; mp: 178-180° C.).

(7) 1-acetyl-5-bromo-3-acetoxyindole 2-(N-carboxymethylamino)-5-bromobenzoic acid (0.84 g, 3.4 mmol) and anhydrous sodium acetate (0.6 g, 7.3 mmol) were dissolved in 8 ml acetic anhydride. After stirred for 5 hours at 60° C., the reaction mixture was cooled down to room temperature. Sodium acetate was filtered off. The filtrate was evaporated, and the residue was dissolved in 100 ml ethyl acetate. 100 ml water and 20 ml saturated sodium bicarbonate were added to the solution, and the organic phase was separated. The aqueous phase was extracted with ethyl acetate (50 ml×2). The combined organic phases were washed with saturated sodium bicarbonate (100 ml×2), dried and evaporated to obtain a white solid (1-acetyl-5-bromo-3-acetoxyindole) (1.3 g, 25.4%).

(8) 1-acetyl-5-bromo-3-hydroxyindole 1-acetyl-5-bromo-3-acetoxyindole (1.0 g, 3.38 mmol) and sodium sulfite (1.0 g, 7.94 mmol) were mixed in 20 ml water. After heated for 3 hours at 80° C., the reaction mixture was cooled down to room temperature, and then extracted with ethyl acetate (50 ml×2). The combined organic phases were dried and evaporated to obtain a solid as white needles (1-acetyl-5-bromo-3-hydroxyindole) (0.7 g, yield: 82%; mp: 180-182° C.).

Example 1-2

Preparation of the Target Compounds (1) 1-methyl-5-azaindirubin (2)

To 1-methyl-5-azaindole-2,3-dione (0.2 g, 1.23 mmol), 1-acetyl-3-hydroxyindole (0.21 g, 1.2 mmol), 20 ml water and 0.02 g of para-toluenesulfonic acid were added. The reaction mixture was stirred and refluxed under nitrogen for 1 hour to get a prunosus solution. After cooling down, the mixture was extracted with trichloromethane, washed with water, and evaporated to give a prunosus solid. The solid was purified by silica gel column chromatography (trichloromethane/petroleum ether, v/v, 3/1), and recrystallized from ethyl to obtain a crystal as red needles (1-methyl-5-azaindirubin (2)) (0.15 g, yield: 44%; mp: 114-116° C.).

ESI-MS: 278.1 [M+H]$^+$, $C_{16}H_{11}N_3O_2$ (277.2);
$^1$H NMR (AV-300, CDCl$_3$, ppm) δ: 3.48 (s, 3H, —CH$_3$), 7.08 (m, 1H, 5'-H), 7.09 (m, 1H, 6'-H), 7.16 (dd, 1H, J=7.6 Hz, 4'-H), 7.76 (d, J=7.6 Hz, 1H, 7'-H), 8.10 (s, 1H, 4-H), 8.26 (dd, J=5.5 Hz; 1H. 6-H), 9.10 (dd, J=5.5 Hz, 1H, 7-H), 10.4 (bs, 1H, N—H);

Anal Calcd for $C_{16}H_{11}N_3O_2$: C, 69.31; H, 3.97; N, 15.16; Found: C, 69.15; H, 4.09; N, 15.29.

(2) 1-benzyl-5'-chloro-5-azaindirubin (19)

Using the method of (1), 1-benzyl-5-azaindole-2,3-dione and 1-acetyl-5-chloro-3-hydroxyindole with the similar molar amount as (1), and 0.02 g of para-toluenesulfonic acid were added to 20 ml water. The reaction mixture was stirred and refluxed under nitrogen for 1 hour to give a prunosus solution. After cooling down, the mixture was extracted with trichloromethane, washed with water, and evaporated to get a prunosus solid. The solid was purified by silica gel column chromatography (trichloromethane/petroleum ether, v/v, 3/1), and recrystallized from ethyl to obtain a crystal as red needles (1-benzyl-5'-chloro-5-azaindirubin (19)) (0.18 g, yield: 39%; mp: 110-112° C.).

ESI-MS: 389 [M+H]$^+$, $C_{22}H_{14}ClN_3O_2$ (387.9);
$^1$H NMR (AV-300, CDCl$_3$, ppm) δ: 5.21 (s, 2H, N—CH$_2$), 10.44 (s, 1H, N—H), 6.91~9.02 (m, 11H, Ar—Hs);

Anal Calcd for $C_{22}H_{14}ClN_3O_2$: C, 68.13; H, 3.64; N, 10.83; Found: C, 68.42; H, 3.59; N, 10.89.

(3) 1-butyl-5-azaindirubin-3'-oxime (40)

1-butyl-5-azaindirubin (0.4 g, 1.25 mmol, prepared by method (1)) was dissolved in 12 ml methanol. 6 ml anhydrous pyridine and hydroxylamine hydrochloride (0.15 g, 2.2 mmol) were added to the solution. The reaction mixture was refluxed for 1 hour, cooled and concentrated to remove most of the solvent. The residue was poured into 100 ml broken ice, stirred vigorously, and filtered to get an orange solid. The solid was purified by silica gel column chromatography (petroleum ether/ethyl acetate, v/v, 3/1), to obtain an orange crystalline powder (1-butyl-5-azaindirubin-3'-oxime (40)) (0.32 g, yield: 90%; mp: 250-252° C.

ESI-MS: 335.1 [M+H]$^+$. $C_{19}H_{18}N_4O_2$ (334.3);
$^1$H NMR (AV-300, D6-DMSO, ppm) δ: 0.91 (t, 3H, —CH$_3$), 1.31 (m, 2H, —CH$_2$), 2.28 (m, 2H, —CH$_2$), 3.28 (m, 2H, N—CH$_2$), 7.10~8.81 (m, 7H, Ar—Hs), 11.71 (s, 1H, N—H), 13.70 (s, 1H, N—OH);

Anal. Calcd. For $C_{19}H_{18}N_4O_2$: C, 68.25; H, 5.43; N, 16.76. Found: C, 68.33; H, 5.56; N, 16.66.

(4) 1-butyl-5-azaindirubin-3'-monooxime O-methyl ether (53)

1-butyl-5-azaindirubin-3'-oxime (1.5 g, 4.5 mmol) was added to 50 ml of 5% KOH in anhydrous ethanol, slightly heated to dissolve, and filtered. 5 ml CH$_3$I was added dropwise into the filtrate with stirred constantly. The reaction released heat, forming a dark red precipitate. After stirred for 0.5 h, the mixture was filtered by pump filter. The precipitate was washed with water to neutral pH, and dried to get a dark red crude product. The crude product was recrystallized from acetone to obtain a dark red crystal (1-butyl-5-azaindirubin-3'-monooxime O-methyl ether (53)) (1.20 g, yield: 77%; mp: 209-211° C.).

ESI-MS: 349.1 [M+H]⁺, $C_{20}H_{20}N_4O$ (348.2);

¹H-NMR (AV-300, D6-DMSO, ppm) δ: 0.98 (t, 3H, —CH₃), 1.46 (m, 2H, —CH₂), 2.08 (m, 2H, —CH₂), 3.86 (m, 2H, N—CH₂), 4.16 (s, 3H, O—CH₃), 7.10~9.19 (m, 7H, Ar—Hs), 10.86 (bs, 1H, N—H);

Anal. Calcd. For $C_{20}H_{20}N_4O_2$: C, 68.95; H, 5.79; N, 16.08. Found: C, 68.81; H, 5.62; N, 15.85.

(5) 1-isopropyl-5-azaisoindigo (73)

1-isopropyl-5-azaindole-2,3-dione (0.4 g, 2.1 mmol) and 2-hydroxyindole (0.28 g, 2.1 mmol) were added to 10 ml ethanol. The mixture was adjusted to pH 9 with 1 mol/L sodium hydroxide, and reacted for 2 hours at 70° C. to get a brown solid. After cooling down, the mixture was filtered by pump filter. The solid was washed with water and ethanol, and dried in vacuum to obtain a reddish brown solid (1-isopropyl-5-azaisoindigo (73)) (0.44 g, yield: 66%; mp: 128-130° C.).

ESI-MS: 306.1 [M+H]⁺, 304.2 [M−H]⁻, $C_{18}H_{15}N_3O_2$ (305.3);

¹H NMR (AV-300, D6-DMSO, ppm) δ: 1.52 (d, 6H, —CH(CH₃)₂), 4.81 (m, 1H, —CH(CH₃)₂), 6.86-9.32 (m, 7H, Ar—Hs), 10.96 (bs, 1H, N—H);

Anal. Calcd. For $C_{18}H_{15}N_3O_2$: C, 70.81; H, 4.95; N, 13.76. Found: C, 70.62; H, 5.10; N, 13.58.

(6) 1-methyl-7-azaindirubin (93)

To 1-methyl-7-azaindole-2,3-dione (0.2 g, 1.23 mmol), 1-acetyl-3-hydroxyindole (0.21 g, 1.2 mmol), 20 ml water and 0.02 g of para-toluenesulfonic acid were added. The reaction mixture was stirred and refluxed under nitrogen for 1 hour to get a prunosus solution. After cooling down, the mixture was extracted with trichloromethane, washed with water, and evaporated to get a prunosus solid. The solid was purified by silica gel column chromatography (trichloromethane/petroleum ether, v/v, 3/1), and further recrystallized from ethyl acetate to obtain a crystal as red needles (1-methyl-7-azaindirubin (93)) (0.14 g, yield: 41.1%; mp: 116-118° C.).

ESI-MS: 278.1 [M+H]⁺, $C_{16}H_{11}N_3O_2$ (277.2);

¹H NMR (AV-300, CDCl₃, ppm) δ: 3.59 (s, 3H, —CH₃), 7.08 (m, 1H, 5'-H), 7.09 (m, 1H, 6'-H), 7.16 (dd, 1H, J=7.6 Hz, 4-H), 7.58 (m, 1H, 5-H), 7.76 (d, J=7.6 Hz, 1H, 7'-H), 8.21 (dd, J=5.5 Hz, 1H, 4-H), 9.13 (dd, J=5.5 Hz, 1H, 6-H), 10.4 (bs, 1H, N—H);

Anal Calcd for $C_{16}H_{11}N_3O_2$: C, 69.31; H, 3.97; N, 15.16; Found: C, 69.05; H, 4.18; N, 15.34.

(7) 1-benzyl-5'-bromo-7-azaindirubin (109)

Using the method of (6), 1-benzyl-7-azaindole-2,3-dione and 1-acetyl-5-bromo-3-hydroxyindole with the similar molar amount as (6), and 0.02 g of para-toluenesulfonic acid were added to 20 ml water. The reaction mixture was stirred and refluxed under nitrogen for 1 hour to get a prunosus solution. After cooling down, the mixture was extracted with trichloromethane, washed with water, and evaporated to get a prunosus solid. The solid was purified by silica gel column chromatography (trichloromethane/petroleum ether, v/v, 3/1), and recrystallized from ethyl acetate to obtain a crystal as red needles (1-benzyl-5'-bromo-7-azaindirubin (109)) (0.14 g, yield: 27%; mp: 112-114° C.).

ESI-MS: 433 [M+H]⁺, $C_{22}H_{14}BrN_3O_2$ (432.2);

¹H NMR (AV-300, CDCl₃, ppm) δ: 5.24 (s, 2H, N—CH₂), 10.44 (s, 1H, N—H), 6.91~9.0 (m, 11H, Ar—Hs);

Anal Calcd for $C_{22}H_{14}BrN_3O_2$: C, 61.13; H, 3.26; N, 9.72; Found: C, 60.72; H, 3.57; N, 9.38.

(8) 1-butyl-7-azaindirubin-3'-oxime (131)

1-butyl-7-azaindirubin (0.4 g, 1.25 mmol, prepared by method (6)) was dissolved in 12 ml methanol. 6 ml anhydrous pyridine and (0.15 g, 2.2 mmol) hydroxylamine hydrochloride were added to the solution. The reaction mixture was heated reflux for 1 hour, then cooled down and concentrated to remove most of the solvent. The residue was poured into 100 ml broken ice, stirred vigorously, and filtered to get an orange solid. The solid was purified by silica gel column chromatography (petroleum ether/ethyl acetate, v/v, 3/1), to obtain an orange solid (1-butyl-7-azaindirubin-3'-oxime (131)) (0.31 g, yield: 87.7%; mp: 254-256° C.).

ESI-MS: 335.1 [M+H]⁺, $C_{19}H_{18}N_4O_2$ (334.3);

¹H NMR(AV-300, D6-DMSO, ppm) δ: 0.92 (t, 3H, —CH₃), 1.31 (m, 2H, —CH₂), 2.28 (m, 2H, —CH₂), 3.32 (m, 2H, N—CH₂), 7.03~8.81 (m, 7H, Ar—Hs), 11.7 (s, 1H, N—H), 13.7 (s, 1H, N—OH);

Anal. Calcd. For $C_{19}H_{18}N_4O_2$: C, 68.25; H, 5.43; N, 16.76. Found: C, 68.09; H, 5.60; N, 16.58.

(9) 1-butyl-7-azaindirubin-3'-monooxime O-methyl ether (144)

1-butyl-7-azaindirubin-3'-oxime (1.5 g, 4.5 mmol) was added to 50 ml of 5% KOH in anhydrous ethanol, slightly heated to dissolve, and filtered. 5 ml CH₃I was added dropwise into the filtrate with stirring constantly. The reaction released heat, forming a dark red precipitation. After stirred for 0.5 h, the mixture was filtered by pump filter. The precipitate was washed with water to neutral pH, and dried to get a dark red crude product. The crude product was recrystallized from acetone to obtain a dark red crystal (1-butyl-7-azaindirubin-3'-monooxime O-methyl ether (144)) (1.26 g, yield 80.5%; mp: 212-214° C.).

ESI-MS: 349.1 [M+H]⁺, $C_{20}H_{20}N_4O$ (348.2);

¹H-NMR (AV-300, D6-DMSO, ppm) δ: 0.98 (t, 3H, —CH₃), 1.46 (m, 2H, —CH₂), 2.08 (m, 2H, —CH₂), 3.88 (m, 2H, N—CH₂), 4.16 (s, 3H, O—CH₃), 7.06~9.19 (m, 7H, Ar—Hs), 10.86 (bs, 1H, N—H);

Anal. Calcd. For $C_{20}H_{20}N_4O_2$: C, 68.95; H, 5.79; N, 16.08. Found: C, 68.79; H, 5.59; N, 15.88.

(10) 1-isopropyl-7-azaisoindigo (164)

1-isopropyl-7-azaindole-2,3-dione (0.4 g, 2.1 mmol) and 2-hydroxyindole (0.28 g, 2.1 mmol) were added to 10 ml ethanol. The mixture was adjusted to pH 9 with 1 mol/L sodium hydroxide, and reacted for 2 hours at 70° C. to get a brown solid. After cooling down, the mixture was filtered by pump filter. The solid was washed with water and ethanol, and dried in vacuum to obtain a reddish brown solid (1-isopropyl-7-azaisoindigo (164)) (0.42 g, yield: 63.2%; mp: 132-134° C.).

ESI-MS: 306.1 [M+H]⁺, 304.2 [M−H]⁻, $C_{18}H_{15}N_3O_2$ (305.3);

¹H NMR (AV-300, D6-DMSO, ppm) δ: 1.51 (d, 6H, —CH(CH₃)₂), 4.78 (m, 1H, —CH(CH₃)₂), 6.86-9.3 (m, 7H, Ar—Hs), 10.99 (bs, 1H, N—H);

Anal. Calcd. For $C_{18}H_{15}N_3O_2$: C, 70.81; H, 4.95; N, 13.76. Found: C, 70.53; H, 5.04; N, 13.52.

59 5-azaindirubin compounds (1) were prepared according to the methods for preparing 5-azaindirubin derivatives such as compound Nos. 2, 19, 40 and 53. Their structures are shown in Table 1. The structures of all the new compounds were confirmed by mass spectrometry (ESI-MS), hydrogen spectrum ($^1$H-NMR) and elemental analysis, and a portion of them were further confirmed by infrared spectrum (IR), ultraviolet spectrum (UV/VIS).

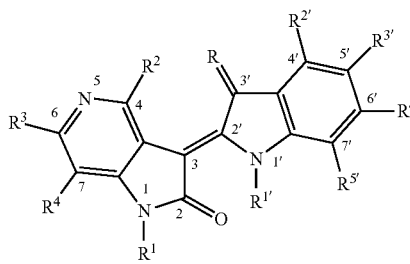

I

Wherein, $R^2$~$R^4$, $R^{1'}$, $R^{2'}$, $R^{4'}$ and $R^{5'}$ represent H, and the other are shown in table 1.

TABLE 1

The structures of 5-azaindirubin derivatives (I)

| Nos | $R^1$ | $R^{3'}$ | R |
|---|---|---|---|
| 1 | H | H | O |
| 2 | CH$_3$ | H | O |
| 3 | CH$_3$ | OH | O |
| 4 | CH$_3$ | OCH$_3$ | O |
| 5 | CH$_3$ | SCH$_3$ | O |
| 6 | C$_2$H$_5$ | H | O |
| 7 | i-C$_3$H$_7$ | H | O |
| 8 | n-C$_4$H$_9$ | H | O |
| 9 | CH$_2$—Ph | H | O |
| 10 | CH$_3$ | Br | O |
| 11 | CH$_3$ | Cl | O |
| 12 | C$_2$H$_5$ | Br | O |
| 13 | C$_2$H$_5$ | Cl | O |
| 14 | i-C$_3$H$_7$ | Br | O |
| 15 | i-C$_3$H$_7$ | Cl | O |
| 16 | n-C$_4$H$_9$ | Br | O |
| 17 | n-C$_4$H$_9$ | Cl | O |
| 18 | CH$_2$—Ph | Br | O |
| 19 | CH$_2$—Ph | Cl | O |
| 20 | CH$_2$—Ph | F | O |
| 21 | triacetylribosyl | H | O |
| 22 | PhCO | OCH$_3$ | S |
| 23 | CH$_3$CH$_2$CO | OCH$_3$ | S |
| 24 | CH$_3$ | Br | N—OH |
| 25 | CH$_3$ | Cl | N—OH |
| 26 | CH$_3$ | Ph | N—OH |
| 27 | CH$_3$ | SCH$_3$ | N—OH |
| 28 | C$_2$H$_5$ | Br | N—OH |
| 29 | C$_2$H$_5$ | Cl | N—OH |
| 30 | i-C$_3$H$_7$ | Br | N—OH |
| 31 | i-C$_3$H$_7$ | Cl | N—OH |
| 32 | n-C$_4$H$_9$ | Br | N—OH |
| 33 | n-C$_4$H$_9$ | Cl | N—OH |
| 34 | CH$_2$—Ph | Br | N—OH |
| 35 | CH$_2$—Ph | Cl | N—OH |
| 36 | CH$_2$—Ph | F | N—OH |
| 37 | CH$_3$ | H | N—OH |
| 38 | C$_2$H$_5$ | H | N—OH |
| 39 | i-C$_3$H$_7$ | H | N—OH |
| 40 | n-C$_4$H$_9$ | H | N—OH |
| 41 | CH$_2$—Ph | H | N—OH |
| 42 | ribosyl | H | N—OH |
| 43 | glucosyl | H | N—OH |
| 44 | CH$_3$ | H | N—OCH$_3$ |
| 45 | CH$_3$ | Br | N—OCH$_3$ |
| 46 | CH$_3$ | Cl | N—OCH$_3$ |
| 47 | C$_2$H$_5$ | H | N—OCH$_3$ |
| 48 | C$_2$H$_5$ | Br | N—OCH$_3$ |
| 49 | C$_2$H$_5$ | Cl | N—OCH$_3$ |
| 50 | i-C$_3$H$_7$ | H | N—OCH$_3$ |
| 51 | i-C$_3$H$_7$ | Br | N—OCH$_3$ |
| 52 | i-C$_3$H$_7$ | Cl | N—OCH$_3$ |
| 53 | n-C$_4$H$_9$ | H | N—OCH$_3$ |
| 54 | n-C$_4$H$_9$ | Br | N—OCH$_3$ |
| 55 | n-C$_4$H$_9$ | Cl | N—OCH$_3$ |
| 56 | CH$_2$—Ph | H | N—OCH$_3$ |
| 57 | CH$_2$—Ph | F | N—OCH$_3$ |
| 58 | CH$_2$—Ph | Br | N—OCH$_3$ |
| 59 | CH$_2$—Ph | Cl | N—OCH$_3$ |

30 5-azaisoindigo compounds (II) were prepared according to the methods for preparing 1-isopropyl-5-azaisoindigo (73). Their structures are shown in Table 2. The structures of all the new compounds were confirmed by infrared spectrum (IR), ultraviolet spectrum (UV/VIS), mass spectrometry (ESI-MS), hydrogen spectrum ($^1$H-NMR) and elemental analysis.

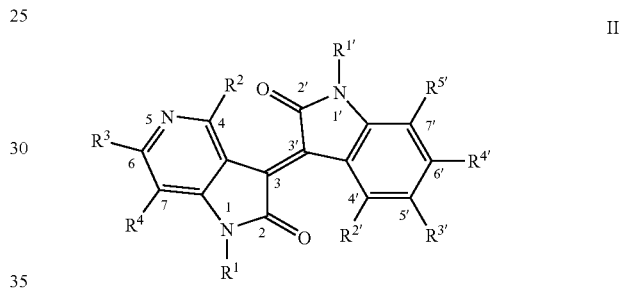

II

Wherein, $R^2$~$R^4$, $R^{2'}$, $R^{4'}$ and $R^{5'}$ represent H, and the other are shown in table 2.

TABLE 2

The structures of 5-azaisoindigo derivatives (II)

| Nos | $R^1$ | $R^{1'}$ | $R^{3'}$ |
|---|---|---|---|
| 60 | CH$_3$ | H | H |
| 61 | CH$_3$ | H | Br |
| 62 | CH$_3$ | H | Cl |
| 63 | CH$_3$ | H | F |
| 64 | CH$_3$ | CH$_3$ | OH |
| 65 | CH$_3$CH$_2$CO | H | OCH$_3$ |
| 66 | PhCO | H | OCH$_3$ |
| 67 | triacetylribosyl | H | H |
| 68 | C$_2$H$_5$ | H | H |
| 69 | C$_2$H$_5$ | C$_2$H$_5$ | Br |
| 70 | C$_2$H$_5$ | H | Cl |
| 71 | C$_2$H$_5$ | H | F |
| 72 | C$_2$H$_5$ | C$_2$H$_5$ | OH |
| 73 | i-C$_3$H$_7$ | H | H |
| 74 | i-C$_3$H$_7$ | H | Br |
| 75 | i-C$_3$H$_7$ | H | Cl |
| 76 | i-C$_3$H$_7$ | H | F |
| 77 | i-C$_3$H$_7$ | i-C$_3$H$_7$ | OH |
| 78 | n-C$_4$H$_9$ | H | H |
| 79 | n-C$_4$H$_9$ | H | Br |
| 80 | n-C$_4$H$_9$ | H | Cl |
| 81 | n-C$_4$H$_9$ | i-C$_4$H$_9$ | OH |
| 82 | n-C$_4$H$_9$ | H | F |
| 83 | n-C$_4$H$_9$ | n-C$_4$H$_9$ | OCH$_3$ |
| 84 | CH$_2$—Ph | H | H |
| 85 | CH$_2$—Ph | H | Br |
| 86 | CH$_2$—Ph | CH$_2$—Ph | Cl |

TABLE 2-continued

The structures of 5-azaisoindigo derivatives (II)

| Nos | $R^1$ | $R^{1'}$ | $R^{3'}$ |
|---|---|---|---|
| 87 | $CH_2$—Ph | H | F |
| 88 | $CH_2$—Ph | $CH_2$—Ph | OH |
| 89 | ribosyl | H | H |

59 7-azaindirubin compounds (III) were prepared according to the methods for preparing 7-azaindirubin derivatives such as compound Nos. 93, 109, 131 and 144. Their structures are shown in Table 3. The structures of all the new compounds were confirmed by mass spectrometry (ESI-MS), hydrogen spectrum ($^1$H-NMR) and elemental analysis, and a portion of them were further confirmed by infrared spectrum (IR), ultraviolet spectrum (UV/VIS).

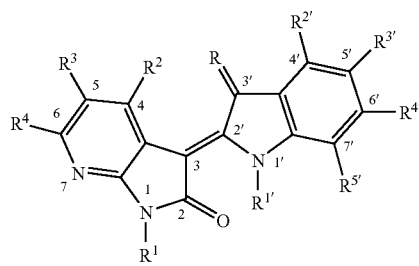

III

Wherein, $R^2$, $R^4$, $R^{1'}$, $R^{2'}$, $R^{4'}$ and $R^{5'}$ represent H, and the other are shown in table 3.

TABLE 3

The structures of 7-azaindirubin derivatives (III)

| Nos | $R^1$ | $R^3$ | $R^{3'}$ | R |
|---|---|---|---|---|
| 92 | H | H | H | O |
| 93 | $CH_3$ | H | H | O |
| 94 | $CH_3$ | $CH_3$ | OH | O |
| 95 | $CH_3$ | $CH_3$ | $OCH_3$ | O |
| 96 | $CH_3$ | $CH_3$ | $SCH_3$ | O |
| 97 | $C_2H_5$ | H | H | O |
| 98 | i-$C_3H_7$ | H | H | O |
| 99 | n-$C_4H_9$ | H | H | O |
| 100 | $CH_2$—Ph | H | H | O |
| 101 | $CH_3$ | H | Br | O |
| 102 | $CH_3$ | H | Cl | O |
| 103 | $C_2H_5$ | H | Br | O |
| 104 | $C_2H_5$ | H | Cl | O |
| 105 | i-$C_3H_7$ | H | Br | O |
| 106 | i-$C_3H_7$ | H | Cl | O |
| 107 | n-$C_4H_9$ | H | Br | O |
| 108 | n-$C_4H_9$ | H | Cl | O |
| 109 | $CH_2$—Ph | H | Br | O |
| 110 | $CH_2$—Ph | H | Cl | O |
| 111 | $CH_2$—Ph | $NHCH_3$ | F | O |
| 112 | triacetylribosyl | $CH_3$ | H | O |
| 113 | PhCO | $CH_3$ | $OCH_3$ | S |
| 114 | $CH_3CH_2CO$ | F | $OCH_3$ | S |
| 115 | $CH_3$ | H | Br | N—OH |
| 116 | $CH_3$ | H | Cl | N—OH |
| 117 | $CH_3$ | $CF_3$ | Ph | N—OH |
| 118 | $CH_3$ | $CH_3$ | $SCH_3$ | N—OH |
| 119 | $C_2H_5$ | H | Br | N—OH |
| 120 | $C_2H_5$ | H | Cl | N—OH |
| 121 | i-$C_3H_7$ | H | Br | N—OH |
| 122 | i-$C_3H_7$ | H | Cl | N—OH |
| 123 | n-$C_4H_9$ | H | Br | N—OH |
| 124 | n-$C_4H_9$ | H | Cl | N—OH |
| 125 | $CH_2$—Ph | H | Br | N—OH |

TABLE 3-continued

The structures of 7-azaindirubin derivatives (III)

| Nos | $R^1$ | $R^3$ | $R^{3'}$ | R |
|---|---|---|---|---|
| 126 | $CH_2$—Ph | H | Cl | N—OH |
| 127 | $CH_2$—Ph | H | F | N—OH |
| 128 | $CH_3$ | H | H | N—OH |
| 129 | $C_2H_5$ | H | H | N—OH |
| 130 | i-$C_3H_7$ | H | H | N—OH |
| 131 | n-$C_4H_9$ | H | H | N—OH |
| 132 | $CH_2$—Ph | H | H | N—OH |
| 133 | ribosyl | $CH_3$ | H | N—OH |
| 134 | glucosyl | $CH_3$ | H | N—OH |
| 135 | $CH_3$ | H | H | N—$OCH_3$ |
| 136 | $CH_3$ | H | Br | N—$OCH_3$ |
| 137 | $CH_3$ | H | Cl | N—$OCH_3$ |
| 138 | $C_2H_5$ | H | H | N—$OCH_3$ |
| 139 | $C_2H_5$ | H | Br | N—$OCH_3$ |
| 140 | $C_2H_5$ | H | Cl | N—$OCH_3$ |
| 141 | i-$C_3H_7$ | H | H | N—$OCH_3$ |
| 142 | i-$C_3H_7$ | H | Br | N—$OCH_3$ |
| 143 | i-$C_3H_7$ | H | Cl | N—$OCH_3$ |
| 144 | n-$C_4H_9$ | H | H | N—$OCH_3$ |
| 145 | n-$C_4H_9$ | H | Br | N—$OCH_3$ |
| 146 | n-$C_4H_9$ | H | Cl | N—$OCH_3$ |
| 147 | $CH_2$—Ph | H | H | N—$OCH_3$ |
| 148 | $CH_2$—Ph | H | F | N—$OCH_3$ |
| 149 | $CH_2$—Ph | H | Br | N—$OCH_3$ |
| 150 | $CH_2$—Ph | H | Cl | N—$OCH_3$ |

30 5-azaisoindigo compounds (IV) were prepared according to the methods for preparing 1-isopropyl-7-azaisoindigo (164). Their structures are shown in Table 4. The structures of all the new compounds were confirmed by infrared spectrum (IR), ultraviolet spectrum (UV/VIS), mass spectrometry (ESI-MS), hydrogen spectrum ($^1$H-NMR) and elemental analysis.

IV

Wherein, $R^2$, $R^4$, $R^{2'}$, $R^{4'}$ and $R^{5'}$ represent H, and the other are shown in table 4.

TABLE 4

The structures of 7-azaisoindigo derivatives (IV)

| Nos | $R^1$ | $R^{1'}$ | $R^3$ | $R^{3'}$ |
|---|---|---|---|---|
| 151 | $CH_3$ | H | H | H |
| 152 | $CH_3$ | H | H | Br |
| 153 | $CH_3$ | H | H | Cl |
| 154 | $CH_3$ | H | H | F |
| 155 | $CH_3$ | $CH_3$ | $CH_3$ | OH |
| 156 | $CH_3CH_2CO$ | H | F | $OCH_3$ |
| 157 | PhCO | H | $CH_3$ | $OCH_3$ |
| 158 | triacetylribosyl | H | $CH_3$ | H |
| 159 | $C_2H_5$ | H | H | H |
| 160 | $C_2H_5$ | $C_2H_5$ | H | Br |
| 161 | $C_2H_5$ | H | H | Cl |
| 162 | $C_2H_5$ | H | H | F |
| 163 | $C_2H_5$ | $C_2H_5$ | $CF_3$ | OH |

TABLE 4-continued

The structures of 7-azaisoindigo derivatives (IV)

| Nos | $R^1$ | $R^{1'}$ | $R^3$ | $R^{3'}$ |
|-----|-------|----------|-------|----------|
| 164 | i-$C_3H_7$ | H | H | H |
| 165 | i-$C_3H_7$ | H | H | Br |
| 166 | i-$C_3H_7$ | H | H | Cl |
| 167 | i-$C_3H_7$ | H | $OCH_3$ | F |
| 168 | i-$C_3H_7$ | i-$C_3H_7$ | H | OH |
| 169 | n-$C_4H_9$ | H | H | H |
| 170 | n-$C_4H_9$ | H | H | Br |
| 171 | n-$C_4H_9$ | H | H | Cl |
| 172 | n-$C_4H_9$ | n-$C_4H_9$ | $SCH_3$ | OH |
| 173 | n-$C_4H_9$ | H | H | F |
| 174 | n-$C_4H_9$ | n-$C_4H_9$ | $OCH_3$ | $OCH_3$ |
| 175 | $CH_2$—Ph | H | H | H |
| 176 | $CH_2$—Ph | H | H | Br |
| 177 | $CH_2$—Ph | $CH_2$—Ph | $SCH_3$ | Cl |
| 178 | $CH_2$—Ph | H | $OCH_3$ | F |
| 179 | $CH_2$—Ph | $CH_2$—Ph | H | OH |
| 180 | ribosyl | H | $CH_3$ | H |

Example 2

Tests of the Antitumor Activities (1)

1. Materials and Instruments (i) Cell Lines: androgen-independent human prostate cancer cell lines DU145 were purchased from American Type Culture Collection.

(ii) Reagents: RPMI Medium 1640 (GIBCOBRL, Inc. U.S.A.), calf serum (Hangzhou Sijiqing Biological Engineering Materials Co., Ltd.), MTT (Sigma), HEPES (Shanghai Livzon Pharmaceutical Co., Ltd.), L-glutamine (imported from Japan), dimethyl sulfoxide (DMSO, analytical reagent);

Measured Samples: a portion of the 5-azaindirubin and 5-azaisoindigo derivatives (20 new compounds, in-house), a portion of the 7-azaindirubin and 7-azaisoindigo derivatives (38 new compounds, in-house);

Reference Substances: 1-ethyl-indirubin (90) and 1-ethyl-indirubin-3'-oxime (91), which were prepared in our lab and the structure of which were identified; and all-trans retinoic acid.

(iii) Preparation of Reagents a, Cell Culture Medium: 10.4 g of 1640 medium powder, 2.1 g of sodium bicarbonate, 0.3 g of glutamine, 5.95 g of HEPES, 100,000 units of penicillin and 100,000 units of streptomycin were added to 1000 ml double distilled water. The mixture was sterilized by filtration using millipore filter, and aliquots were stored at −20° C. The inactivated calf serum was added to the medium prior to use.

b, Calf Serum: It was inactivated for 30 minutes in 56° C. water bath, and the aliquots were stored at −20° C.;

c, MTT: It was diluted to 5 mg/ml with PBS, stored at 4° C. and kept away from light. It was used within two weeks;

d, PBS: 8.00 g of sodium chloride, 0.20 g of potassium chloride, 3.4 g disodium phosphate dodecahydrate and 0.20 g of potassium phosphate dibasic were fully dissolved in double distilled water at 37° C., diluted to 1000 ml, and aliquots were stored at 4° C.;

e, 58 measured samples, the reference substances (90 and 91) and all-trans retinoic acid were formulated into solutions in DMSO, and stored at −20° C.

(iv) Main Equipments:

$CO_2$ incubator (GB16, Heraeus company, German); clean bench (SW-CJ-1F, Suzhou Antai Air Tech Co., Ltd.); horizontal centrifuge (LXJ-11, Shanghai Third Medical Instruments Factory); enzyme-linked immune detector (BIO RAD Model 550, USA); inverted biological microscope (XSZ-D2, Chongqing Optical Instrument Factory); rapid mixer (SK-1 type, Changzhou Guohua Electric Appliance Co., Ltd.); electrical heating water thermostat system (DK-8D, Shanghai Medical Constant Temperature Equipment Factory); flow cytometry (FACSCalibur, American BD Company); plate oscillator (752-A, Shanghai Medical Analysis Instrument Factory); electronic balance (BS110S, Sartorius Company, German).

2. Methods (i) Cell Culture

DU145 cells were inoculated in RPM11640 medium containing 10% calf serum, incubated at 37° C., 5% $CO_2$ in $CO_2$ incubator, and passaged every 2-3 days. In this experiment, cells were grown in logarithmic growth phase.

(ii) Grouping

In the experiment, the cells at logarithmic growth phase were formulated into suspension, and the viability by trypan blue staining was more than 98%. The suspension was divided into several groups: 1 as blank control group (cell suspension); and 2 as experimental groups (cell suspension plus drugs).

(iii) Determination of $IC_{50}$ Values by MTT (the 50% Inhibitory Concentration)

The drugs were formulated into a stock solution in DMSO, and the concentration of the stock solution was 20 mmol (used within 4 hours). In the experiment, the work solution of the drugs was diluted with RPM11640 medium containing 10% calf serum under aseptic condition, to a final concentration of 80 µM. The drug concentrations were increased by 2 times (1.25-20 µM).

The DU145 cell in logarithmic growth phase were selected, centrifuged, counted, and formulated into a cell suspension ($2.5 \times 10^4$/ml) with RPM11640 medium containing 10% calf serum. The cell suspension were inoculated into 96-well plates at a density of 5000 cells/200 µl per well, incubated for 24 hours at 37° C., 5% $CO_2$. According to the above concentration of the drug, the cells were inoculated to 6 groups (including one control group), with 8 wells per group. After incubating for 72 hours, the viability of cells was measured by MTT assay. The absorbance value (A) was measured with detection wavelength at 540 nm, reference wavelength at 630 nm. The inhibitory rate (I) was calculated by the following equation, where T was the absorbance value of the experimental groups, and C was the absorbance value of the blank control group:

$I = (1 - T/C) \times 100\%$

Figure 2:
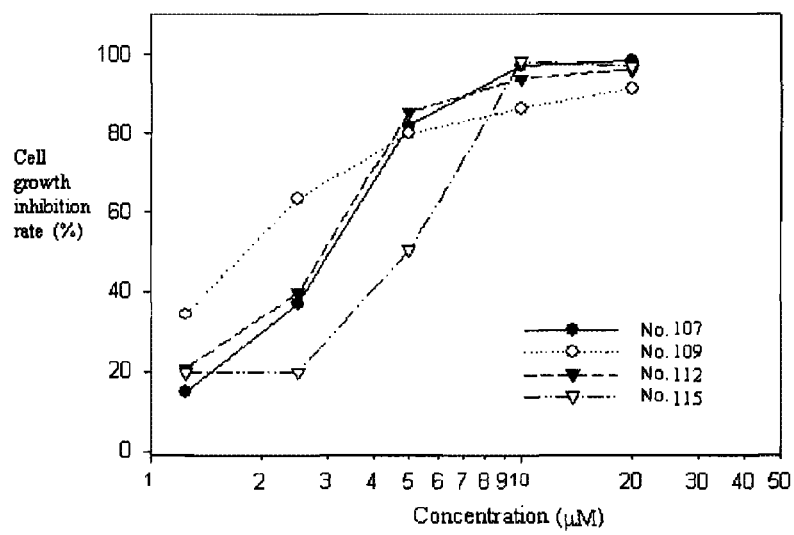
FIG. 2 shows the inhibition rates of growth of androgen-independent human prostate cancer cell lines DU145 by 5- or 7-azaindirubin derivatives and 5- or 7-azaisoindigo derivatives. Human prostate cancer cell lines DU145 in logarithmic growth phase were treated with different concentrations of the compounds No. 107, No. 108, No. 112, No. 115 for 72 hours, and then the cells growth was measured by MTT.

The regression equation was calculated by the concentration-inhibitory rate curve, to obtain 50% and 90% inhibition concentration ($IC_{50}$ and $IC_{90}$, µM). The results are shown in Table 5, Table 6 and FIG. 2.

TABLE 5

$IC_{50}$ and $IC_{90}$ of 5-azaindirubin and 5-azaisoindigo derivatives for inhibiting DU145 tumor cells growth

| No. | $IC_{50}$(µM) | $IC_{90}$(µM) |
|-----|---------------|---------------|
| 7   | >100          | —             |
| 8   | 11.5          | 39.0          |
| 9   | 12.0          | 85.0          |
| 12  | 8.8           | 28.0          |
| 15  | 9.0           | 48.0          |
| 18  | 6.6           | 23.5          |
| 25  | 1.7           | 12.2          |
| 28  | 4.5           | 14.0          |
| 29  | 2.2           | 6.8           |

TABLE 5-continued

IC$_{50}$ and IC$_{90}$ of 5-azaindirubin and 5-azaisoindigo
derivatives for inhibiting DU145 tumor cells growth

| No. | IC$_{50}$(μM) | IC$_{90}$(μM) |
| --- | --- | --- |
| 30 | 3.3 | 7.0 |
| 31 | 3.7 | 11.5 |
| 35 | 7.3 | 20.0 |
| 38 | 6.4 | 22.0 |
| 63 | 48.0 | >100 |
| 67 | 8.0 | 44.0 |
| 71 | 17.0 | 87.0 |
| 75 | 9.7 | 29.0 |
| 78 | 16.0 | 51.0 |
| 79 | 14.5 | 77.0 |
| 82 | >100 | >100 |
| 90 | 7.2 | 31.0 |
| 91 | 4.2 | 21.8 |
| all-trans retinoic acid | >50 | |

TABLE 6

IC$_{50}$ and IC$_{90}$ of 7-azaindirubin and 7-azaisoindigo derivatives
for inhibiting DU145 tumor cells growth

| No. | IC$_{50}$ (μM) | IC$_{90}$(μM) |
| --- | --- | --- |
| 95 | 400 | >100 |
| 98 | >100 | — |
| 99 | 11.5 | 87.0 |
| 100 | 9.5 | 31.5 |
| 101 | 11.5 | 60.0 |
| 102 | 8.0 | 18.0 |
| 103 | 10.0 | 32.2 |
| 104 | 8.5 | 45.0 |
| 105 | 8.1 | 28.5 |
| 106 | 18.5 | 100.0 |
| 107 | 14.0 | 26.0 |
| 108 | 11.0 | 42.0 |
| 109 | 7.0 | 24.0 |
| 111 | 7.4 | 34.0 |
| 116 | 6.9 | 16.0 |
| 119 | 4.0 | 12.0 |
| 120 | 5.4 | 61.0 |
| 121 | 3.1 | 29.0 |
| 122 | 8.0 | 25.0 |
| 123 | 3.7 | 5.0 |
| 124 | 1.8 | 12.0 |
| 126 | 7.1 | 19.0 |
| 128 | 2.7 | 7.1 |
| 129 | 3.8 | 12.0 |
| 130 | 7.05 | 17.0 |
| 131 | 16.0 | 80.0 |
| 154 | 43.0 | >100 |
| 158 | 10.5 | 49.0 |
| 160 | 14.0 | 61.0 |
| 161 | 14.0 | 45.0 |
| 162 | 17.5 | 89.0 |
| 164 | 9.05 | 19.0 |
| 165 | 8.3 | 28.0 |
| 166 | 10.0 | 31.5 |
| 169 | 14.0 | 47.0 |
| 170 | 15.0 | 90.0 |
| 171 | 9.0 | 46.0 |
| 173 | >100 | >100 |

TABLE 6-continued

IC$_{50}$ and IC$_{90}$ of 7-azaindirubin and 7-azaisoindigo derivatives
for inhibiting DU145 tumor cells growth

| No. | IC$_{50}$ (μM) | IC$_{90}$(μM) |
| --- | --- | --- |
| 90 | 7.0 | 30.0 |
| 91 | 4.1 | 22.0 |
| all-trans retinoic acid | >50 | |

Note:
The molecular structures of the control substances are shown as follows:

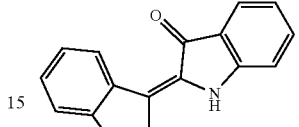

90

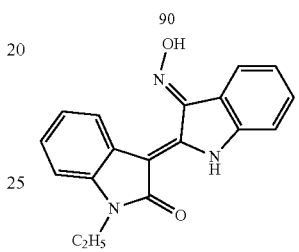

91

3. Discussion (i) From the MTT assay, it is readily found that most of 5- or 7-azaindirubin derivatives and 5- or 7-azaisoindigo derivatives have strong antitumor activity, and the growth inhibitory effects on tumor cells of them are much stronger than that of all-trans retinoic acid, a differentiation inducer. More importantly, most of 5- or 7-azaindirubin derivatives and 5- or 7-azaisoindigo derivatives have good inhibitory effects on androgen-independent human prostate cancer cells DU145 which are clinically refractory;

(ii) The IC$_{50}$ of many 5- or 7-azaindirubin derivatives and 5- or 7-azaisoindigo derivatives are similar to or less than that of the reference substances (90 and 91). Compound 91 is a known CDKs inhibitor[13]. The structures of 38, 129 are quite similar to that of 91, and the difference between them merely involves the atom at 5 or 7-position. It is also suggested that the newly synthesized compounds of the present invention may have similar mechanisms on inhibiting tumor cells growth;

(iii) 3'-oximated and 5'-halogenated 5- or 7-azaindirubin derivatives demonstrate relatively significant growth inhibitory effects on tumor cells, particularly compounds 25, 30, 116, 121 and 124, and compounds 30, 121 and 124 still have good safety profile.

Example 3

Tests of the Antineoplasmic Activities (2)

1. Tumor Cells: human hepatoma cell lines 7701 QGY and HepG-2, human lung adenocarcinoma cell line A549, human chronic myelocytic leukemia cell line K562, human leukemia cell line CEM and mouse melanoma cell line K111.

2. Using the methods described in example 2, the biological activity of a portion of newly synthesized 5- or 7-azaindirubin derivatives and 5- or 7-azaisoindigo derivatives (20 compounds) for inhibiting various tumor cells growth were determined. The 50% inhibitory concentrations (IC$_{50}$, μM) are shown in Table 7.

TABLE 7

IC$_{50}$ (μM) of 5- or 7-azaindirubin and 5- or 7-azaisoindigo derivatives for inhibiting various tumor cells growth

| | IC$_{50}$ (μM) Tumor cells | | | | | |
|---|---|---|---|---|---|---|
| No. | 7701 QGY | HepG-2 | A549 | K562 | CEM | Klll |
| 95 | 23.9 | 50.1 | 35.2 | 8.1 | 9.0 | 15.6 |
| 99 | 12.4 | 29.3 | 18.4 | 6.7 | 7.1 | 10.1 |
| 101 | 15.0 | 28.8 | 21.6 | 7.8 | 12.0 | 23.0 |
| 102 | 39.5 | 41.5 | 22.8 | 9.5 | 7.0 | 18.2 |
| 105 | 13.4 | 32.0 | 24.1 | 19.0 | 8.0 | 11.9 |
| 106 | 28.0 | 18.0 | 19.6 | 20.4 | 10.2 | 14.0 |
| 109 | 10.0 | 21.2 | 15.8 | 12.5 | 9.0 | 18.6 |
| 111 | 28.5 | 17.0 | 24.3 | 15.0 | 11.0 | 15.1 |
| 116 | 11.1 | 20.5 | 12.5 | 8.2 | 5.6 | 6.3 |
| 119 | 13.5 | 8.1 | 8.5 | 7.9 | 9.0 | 8.1 |
| 121 | 14.9 | 16.0 | 18.1 | 11.5 | 11.3 | 6.0 |
| 126 | 11.2 | 16.3 | 9.6 | 5.1 | 8.1 | 14.2 |
| 128 | 7.6 | 12.6 | 10.0 | 7.7 | 10.5 | 3.6 |
| 129 | 7.4 | 13.0 | 14.1 | 3.4 | 7.0 | 4.2 |
| 154 | 36.0 | 29.3 | 12.4 | 19.0 | 9.8 | 12.0 |
| 158 | 44.0 | 18.0 | 22.3 | 5.8 | 12.0 | 8.3 |
| 160 | 25.4 | 31.1 | 29.1 | 10.2 | 10.8 | 15.0 |
| 164 | 33.1 | 29.0 | 23.3 | 18.6 | 12.7 | 9.1 |
| 170 | 28.0 | 25.0 | 19.5 | 10.3 | 8.5 | 18.5 |
| 176 | 13.7 | 20.6 | 13.2 | 4.1 | 7.4 | 8.3 |

The results indicate that 5- or 7-azaindirubin derivatives and 5- or 7-azaisoindigo derivatives have the biological activity of inhibiting various tumor cells growth.

Example 4

Inhibitory Effects on CDKs

Reagents: The tested compounds were the same as example 2. Unless otherwise indicated, other chemical reagents were purchased from Sigma Chemical Company (USA). Polyacrylamide gel used in protein electrophoresis, SDS, electrophoresis buffer, transfer buffer protein, nitrocellulose membrane were purchased from American Bio-Rad Life Science Company. Western blotting detection kits and films were purchased from American GE Company. Phospho-CDK2$^{Thr160}$ antibody, endogenous cyclin-dependent inhibitor p27 antibody, CyclinD1 and β-Actin antibody were purchased from American Cell Signaling Inc., DAKO and Santa Cruz Biochemical Technology Company.

Tumor cells and methods for cell culture were the same as example 2.

Figure 3:
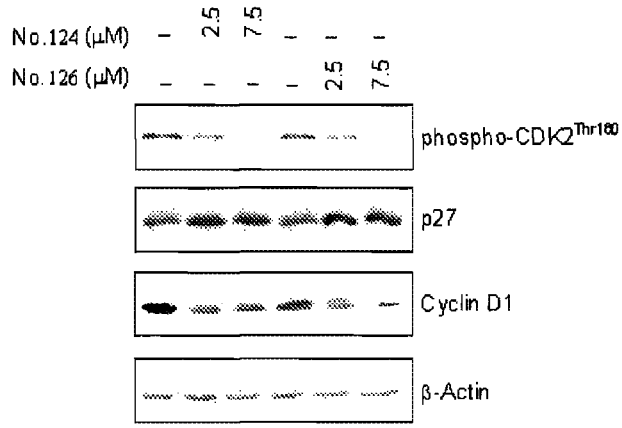
FIG. 3 shows the inhibitory effects of 5- or 7-azaindirubin derivatives and 5- or 7-azaisoindigo derivatives on CDKs in androgen-independent human prostate cancer cell lines DU145. The human prostate cancer cell lines DU145 in logarithmic growth phase were treated with different concentrations of the compounds No. 124, No. 126 for 24 hours. The total proteins were extracted, and then phospho-CDK2$^{Thr160}$, p27 and Cyclin-D1 were determined by Western blotting, with β-actin as an internal standard.

Phospho-Cdc2, p27, and Cyclin D1 were Detected by Western Blot: The human prostate cancer cell lines DU145 at logarithmic growth phase were treated with compounds No. 124 and No. 126 (concentration is shown in FIG. 3) for 24 hours. The cells were harvested and washed. Total cellular proteins were extracted and quantified as described previously[14]. 50 μg of protein was separated on a SDS-PAGE, electro-transferred to nitrocellulose filters. Western blot were performed using specific antibodies against Phospho-CDK2, endogenous cyclin-dependent inhibitor p27 and CyclinD1, with β-Actin antibody as an internal standard. The result was recorded by ECL films.

Results and Discussion:

It is reported that indirubin derivatives can inhibit CDKs of cancer cells. Example 2 and example 3 have demonstrated that 5- or 7-azaindirubin derivatives and 5- or 7-azaisoindigo derivatives of the invention have relatively strong growth inhibitory effects on tumor cells. In order to further elucidate whether these compounds inhibit cell growth by regulating the activity of cyclin-dependent kinases, the effects of the representative compounds in the present invention, No. 124 and No. 126, on the activity of Cdc2 and p27 and the protein expression of cyclin D1 were investigated by Western blot, using specific antibodies against Cdc2 phosphorylation protein and the antibodies against other important proteins which regulate the cell cycle, such as p27 and cyclin D1. As shown in FIG. 3, after treated with compound 124 and 126 for 24 hours, the level of CDK2 activity (phosphorylation) in human prostate cancer cell lines DU145 decreased in a dose-dependent manner. At the same time, the protein expression of cyclin D1 was significantly decreased. In contrast, under the same experimental conditions, the expression of endogenous cyclin-dependent inhibitor p27 was significantly increased. The changes of the signal proteins inhibited the cell growth. The induction of 5- or 7-azaindirubin derivatives and 5- or 7-azaisoindigo derivatives on the expression of p27 may result from the activation of AhR-receptor pathway[15].

Example 5

Studies on Solid Dispersion Preparation

Example 5-1

| | |
|---|---|
| The compound No. 110 in example 1-2 | 5 mg |
| Polyethylene glycol 400 | 50 mg |

Process: To polyethylene glycol 400 melted at 50° C., the compound No. 110 in example 1-2 was added. The mixture was mixed homogeneously, and cured by ice bag quenching while stirring. After dried in the desiccator for 24 h, the mixture was made into dripping pills or capsules according to routine method.

Example 5-2

| | |
|---|---|
| The compound No. 18 in example 1-2 | 5 mg |
| Polyethylene glycol 6000 | 50 mg |
| Lactose - microcrystalline cellulose (10:1) | 1 g |

Process: The compound No. 18 in example 1-2 was dissolved in q.s. alkaline ethanol, and then polyethylene glycol 6000 was added. The mixture was heated at 50° C. to molten and mixed homogeneously, then the excipients (lactose-microcrystalline cellulose (10:1)) were added, and stirred to

Example 5-3

| | |
|---|---|
| The compound No. 18 in example 1-2 | 5 mg |
| Polyvinyl pyrrolidone K-25 | 50 mg |
| Lactose - microcrystalline cellulose (10:1) | 1 g |

Process: The compound No. 18 in example 1-2 was added to q.s. alkaline ethanol, and stirred to dissolve completely. Polyvinyl pyrrolidone K25 was added and stirred to dissolve. The excipients (lactose-microcrystalline cellulose (10:1)) were added, stirred homogeneously. After dried in 60° C. oven for 24 h, the mixture was made into tablets or capsules according to routine method.

Example 5-4

| | |
|---|---|
| The compound No. 31 in example 1-2 | 5 mg |
| Polyoxyethylene (35) castor oil | 350 mg |
| Lactose - microcrystalline cellulose (10:1) | 1 g |

Process: The compound No. 31 in example 1-2 was dissolved in q.s. trichlormethane. Polyoxyethylene (35) castor oil was added and stirred to dissolve. The excipients (lactose-microcrystalline cellulose (10:1)) were added and stirred homogeneously. The mixture was heated at 80° C. using water bath to remove trichlormethane in a fume hood. After dried in 60° C. oven for 24 h, the mixture was made into tablets or capsules according to routine method.

Example 5-5

| | |
|---|---|
| The compound No. 116 in example 1-2 | 5 mg |
| Poloxamer 188 | 100 mg |
| microcrystalline Cellulose | 1 g |

Process: The compound No. 116 in example 1-2 was dissolved in q.s. alkaline ethanol. Poloxamer 188 was added and stirred to dissolve. The excipient (microcrystalline cellulose) was added and stirred homogeneously. After dried in 60° C. oven for 24 h, the mixture was made into tablets or capsules according to routine method.

Example 5-6

| | |
|---|---|
| The compound No. 18 in example 1-2 | 5 mg |
| Poloxamer 188 | 100 mg |
| Polyethylene glycol 6000 | 50 mg |
| Lactose - microcrystalline cellulose (10:1) | 1 g |

Process: The compound No. 18 in example 1-2 was dissolved in q.s. alkaline ethanol. Poloxamer 188 and polyethylene glycol 6000 were added and stirred to dissolve. The excipients (lactose-microcrystalline cellulose (10:1)) were added and stirred homogeneously. After dried in 60° C. oven for 24 h, the mixture was made into tablets or capsules according to routine method.

Example 5-7

| | |
|---|---|
| The compound No. 119 in example 1-2 | 5 mg |
| Polyvinyl pyrrolidone K25 | 50 mg |
| Poloxamer 188 | 50 mg |
| Polyethylene glycol 6000 | 50 mg |
| Lactose | 1 g |

Process: The compound No. 119 in example 1-2 was dissolved in q.s. alkaline ethanol. Poloxamer 188, polyethylene glycol 6000 and polyvinyl pyrrolidone K25 were added and stirred to dissolve. The excipient (lactose) was added and stirred homogeneously. After dried in 60° C. oven for 24 h, the mixture was made into tablets or capsules according to routine method.

Example 5-8

| | |
|---|---|
| The compound No. 18 in example 1-2 | 5 mg |
| Polyvinyl pyrrolidone K25 | 50 mg |
| Poloxamer 188 | 100 mg |
| Polyethylene glycol 6000 | 100 mg |
| Lactose - microcrystalline cellulose (10:1) | 1 g |

Process: The compound No. 18 in example 1-2 was dissolved in q.s. alkaline ethanol. Poloxamer 188, polyethylene glycol 6000 and polyvinyl pyrrolidone K25 were added and stirred to dissolve. The excipients (lactose-microcrystal line cellulose (10:1)) were added and stirred homogeneously. After dried in 60° C. oven for 24 h, the mixture was made into tablets or capsules according to routine method.

Example 5-9

| | |
|---|---|
| The compound No. 29 in example 1-2 | 5 mg |
| Polyoxyethylene (40) castor oil | 750 mg |
| Polyethylene glycol 4000 | 50 mg |

Process: The compound No. 29 in example 1-2 was dissolved in polyoxyethylene (40) castor oil/ethanol solution. Polyethylene glycol 4000 was added. The mixture was stirred to dissolve at 50° C., and cured by ice bag quenching after the solvent was removed. After dried in 60° C. oven for 24 h, the solid was made into tablets or capsules according to routine method.

Example 5-10

| | |
|---|---|
| The compound No. 121 in example 1-2 | 5 mg |
| Polyoxyethylene (40) hydrogenated castor oil | 350 mg |
| Polyvinyl pyrrolidone K25 | 50 mg |
| Lactose - microcrystalline cellulose (7:3) | 1 g |

Process: The compound No. 121 in example 1-2 was dissolved in polyoxyethylene (40) hydrogenated castor oil/ethanol solution. Polyvinyl pyrrolidone K25 was added and stirred to dissolve. The excipients (lactose-microcrystalline cellulose (7:3)) were added and stirred homogeneously. After freeze-dried at −50° C. for 24 h, the mixture was made into tablets or granules according to routine method.

Example 5-11

| | |
|---|---|
| The compound No. 18 in example 1-2 | 5 mg |
| Polyoxyethylene (40) castor oil | 350 mg |
| Polyvinyl pyrrolidone K25 | 50 mg |
| Sodium dodecyl sulfate | 10 mg |
| Lactose - microcrystalline cellulose (10:1) | 1 g |

Process: Polyoxyethylene (40) castor oil and sodium dodecyl sulfate were dissolved in q.s. ethanol. After the two substances completely dissolved, the compound No. 18 in example 1-2 was added and stirred to dissolve completely. Polyvinyl pyrrolidone K25 was then added and stirred to dissolve. The excipients (lactose-microcrystalline cellulose (10:1)) were added and stirred homogeneously. After dried in 60° C. oven for 24 h, the mixture was made into dripping pills according to routine method.

Example 5-12

| | |
|---|---|
| The compound No. 18 in example 1-2 | 5 mg |
| Polyoxyethylene (40) castor oil | 350 mg |
| Polyvinyl pyrrolidone K17 | 50 mg |
| Lactose - microcrystalline cellulose (10:1) | 1 g |

Process: The compound No. 18 in example 1-2 was dissolved in polyoxyethylene (40) castor oil/ethanol solution. Polyvinyl pyrrolidone K17 was added and stirred to dissolve. The excipients (lactose-microcrystalline cellulose (10:1)) were then added and stirred homogeneously. After dried in 60° C. oven for 24 h, the solid was made into tablets or capsules according to routine method.

Example 5-13

| | |
|---|---|
| The compound No. 34 in example 1-2 | 5 mg |
| Vitamin E polyethylene glycol succinate | 350 mg |
| Polyvinyl pyrrolidone K90 | 50 mg |
| Lactose - microcrystalline cellulose (5:5) | 1 g |

Process: The compound No. 34 in example 1-2 was dissolved in vitamin E polyethylene glycol succinate/ethanol solution. Polyvinyl pyrrolidone K90 was added and stirred to dissolve. The excipients (lactose-microcrystalline cellulose (5:5)) were then added and stirred homogeneously. After dried in 60° C. oven for 24 h, the solid was made into tablets or capsules according to routine method.

Example 6

Investigation on the Dissolution of a Portion of Solid Dispersion Preparations

Instruments: RCZ-5A capacity medicament dissolve and infiltrate apparatus is made by Tianjin University Precision Instruments Factory. UV1900 UV-Vis spectrophotometer is made by Shanghai Yayan Electronic Science And Technology Co., Ltd.

Dissolution determination methods: According to the third method of XC dissolution assay stated in the appendix of Chinese Pharmacopeia (Edition 2005), the rotation speed was 100 r/min, the temperature was 37±0.5° C., and the dissolution medium was 100 ml of 1% sodium dodecyl sulfate solution degassed ultrasonically. A specimen was withdrawn at 45 minute and immediately filtered through a 0.8 μm water membrane. The filtrate was quantitatively diluted. The absorbance was measured by UV1900, and the dissolution percentage was calculated.

Results and Discussion:

The dissolution rates of a portion of solid dispersions in the above examples were investigated. The results are shown in table 8.

TABLE 8

Comparison of the dissolutions of a portion of solid dispersion preparations

| Example | Dissolution percentages (%) |
|---|---|
| The compound No. 18 in example 1-2 | 4 |
| 5-2 | 27 |
| 5-3 | 40 |
| 5-6 | 15 |
| 5-8 | 56 |
| 5-11 | 71 |
| 5-12 | 92 |

As shown in the above table, the solid dispersion preparations, which are made from the compounds of the present invention, overcomes the shortcomings of these compounds, such as poor hydrophilicity and being difficult to make into appropriate preparations. Since the dissolution of the compound has been significantly improved, the preparations with practical values could be achieved. The solubilization effect of the solid dispersion preparations using combined carriers is better than that of the solid dispersion preparations using single carrier, because of synergistic effects of more than one carriers. The dissolution of the corresponding dispersion is much better.

Example 7

Investigation on Injections

Example 7-1

| | |
|---|---|
| The compound No. 18 in example 1-2 | 10 mg |
| Medium chain triglyceride | 400 mg |
| Lecithin | 200 mg |
| Glycerine | 225 mg |
| Poloxamer 188 | 200 mg |

Process: The following operations were performed in a laminar flow bacteria free room.

Oil Phase: The compound No. 18 in example 1-2 was added to dimethyl sulfoxide and heated hypothermally to dissolve. Medium chain triglyceride and lecithin were added. The mixture was heated hypothermally while stirred and mixed homogeneously;

Water Phase: Glycerine and poloxamer 188 were added to q.s. injection water and heated. While stirring vigorously, the oil phase was added to the oil phase slowly, and the mixture was stirred vigorously for another 3 minutes. The organic solvent was removed with a rotary evaporator under low temperature.

The prepared emulsion was sterilized through filtration, injected into xi-lin bottles for freeze-drying in a laminar flow bacteria free room. The emulsion was freeze-dried and sealed using a stopper and aluminum cover.

Example 7-2

| | |
|---|---|
| The compound No. 25 in example 1-2 | 10 mg |
| Glyceryl monooleate | 500 mg |
| Phospholipid | 300 mg |
| Glycerine | 225 mg |
| Poloxamer 188 | 200 mg |

Process: The following operations were completed in a laminar flow bacteria free room.

Oil Phase: The compound No. 25 in example 1-2 was added to dimethyl sulfoxide and heated hypothermally to dissolve. Glyceryl monooleate was added and heated to dissolve. Then phospholipid was added, and heated hypothermally to mix homogeneously;

Water Phase: Glycerine and poloxamer 188 were added to q.s. injection water and heated. While stirring vigorously, the oil phase was added to the oil phase slowly, and the mixture was stirred vigorously for another 3 minutes. The organic solvent was removed with a rotary evaporator under low temperature.

The prepared emulsion was sterilized through filtration, injected into xi-lin bottles for freeze-drying in a laminar flow bacteria free room. The emulsion was freeze-dried and sealed using a stopper and aluminum cover.

Example 7-3

| | |
|---|---|
| The compound No. 34 in example 1-2 | 16 mg |
| 20% human albumin | 1 ml |

Process: The following operations were completed in a laminar flow bacteria free room.

Oil Phase: The compound No. 34 in example 1-2 was added to tetrahydrofuran and dichlormethane mixed solution, and heated hypothermally to dissolve.

Water Phase: The human albumin solution was added to the oil phase. The mixture was mixed by ultrasound for 1 min. The organic solvent was removed with a rotary evaporator under low temperature.

The prepared emulsion was sterilized through filtration, injected into xi-lin bottles for freeze-drying in a laminar flow bacteria free room. The emulsion was freeze-dried and sealed using a stopper and aluminum cover.

Example 7-4

| | |
|---|---|
| The compound No. 122 in example 1-2 | 10 mg |
| Polyethylene glycol 400 | 100 mg |
| Lecithin | 50 mg |
| Hydroxypropyl-β-cyclodextrin | 200 mg |

Process: The following operations were completed in a laminar flow bacteria free room.

Oil Phase: The compound No. 122 in example 1-2 was dissolved in alkaline ethanol. Lecithin and polyethylene glycol 400 were added and stirred to dissolve.

Water Phase: Hydroxypropyl-β-cyclodextrin was dissolved in 70% ethanol. The water phase was added to the oil phase, and then q.s. injection water was added and mixed homogeneously. The organic solvent was removed with a rotary evaporator under low temperature.

The prepared emulsion was sterilized through filtration, injected into xi-lin bottles for freeze-drying in a laminar flow bacteria free room. The emulsion was freeze-dried and sealed using a stopper and aluminum cover.

Example 7-5

| | |
|---|---|
| The compound No. 110 in example 1-2 | 10 mg |
| Poloxamer 188 | 200 mg |
| Lecithin | 30 mg |
| Hydroxypropyl-β-cyclodextrin | 300 mg |
| 0.9% sodium chloride solution | 10 ml |

Process: The following operations were completed in a laminar flow bacteria free room.

The compound No. 110 in example 1-2 was dissolved in alkaline ethanol. Poloxamer 188 was added. The mixture was heated with stirring to dissolve, and then cooled down. 0.9% sodium chloride solution and q.s. ethanol were added, and then lecithin was added and mixed homogeneously. Hydroxypropyl-β-cyclodextrin was added. The mixture was mixed homogeneously by ultrasound for 1 min. The organic solvent was removed with a rotary evaporator under low temperature.

The prepared emulsion was sterilized through filtration, injected into xi-lin bottles for freeze-drying in a laminar flow bacteria free room. The emulsion was freeze-dried and sealed using a stopper and aluminum cover.

Example 7-6

| | |
|---|---|
| The compound No. 30 in example 1-2 | 10 mg |
| Poloxamer 188 | 200 mg |
| Soybean phospholipid | 20 mg |
| Hydroxypropyl-β-cyclodextrin | 400 mg |

Process: The following operations were completed in a laminar flow bacteria free room.

The compound No. 30 in example 1-2 was dissolved in alkaline ethanol. Soybean phospholipid and poloxamer 188 were added. Hydroxypropyl-β-cyclodextrin was added. Injection water and q.s. ethanol were added. The organic solvent was removed with a rotary evaporator under low temperature.

The prepared emulsion was sterilized through filtration, injected into xi-lin bottles for freeze-drying in a laminar flow

Example 7-7

| | |
|---|---|
| The compound No. 18 in example 1-2 | 10 mg |
| Polyethylene glycol monolaurate | 200 mg |
| Lecithin | 20 mg |
| Hydroxypropyl-β-cyclodextrin | 200 mg |

Process: The following operations were completed in a laminar flow bacteria free room.

Oil Phase: The compound No. 18 in example 1-2 was dissolved in alkaline ethanol. Lecithin and polyethylene glycol monolaurate were added. The mixture was stirred to dissolve completely.

Water Phase: Hydroxypropyl-β-cyclodextrin was dissolved in 70% ethanol. The water phase was added to the oil phase, and mixed. The organic solvent was removed with a rotary evaporator under low temperature.

The prepared emulsion was sterilized through filtration, injected into xi-lin bottles for freeze-drying in a laminar flow bacteria free room. The emulsion was freeze-dried and sealed using a stopper and aluminum cover.

Example 7-8

| | |
|---|---|
| The compound No. 19 in example 1-2 | 10 mg |
| Polyoxyethylene (40) castor oil | 100 mg |
| Lecithin | 50 mg |
| Hydroxypropyl-β-cyclodextrin | 200 mg |

Process: The following operations were completed in a laminar flow bacteria free room.

Oil Phase: The compound No. 19 in example 1-2 was dissolved in alkaline ethanol. Lecithin and polyoxyethylene (40) castor oil were added. The mixture was stirred to dissolve.

Water Phase: Hydroxypropyl-β-cyclodextrin was dissolved in 70% ethanol. The water phase was added to the oil phase, and q.s. injection water was added and mixed homogeneously. The organic solvent was removed with a rotary evaporator under low temperature.

The prepared emulsion was sterilized through filtration, injected into xi-lin bottles for freeze-drying in a laminar flow bacteria free room. The emulsion was freeze-dried and sealed using a stopper and aluminum cover.

Example 7-9

| | |
|---|---|
| The compound No. 18 in example 1-2 | 20 mg |
| 20% human albumin | 5 ml |

Process: The following operations were completed in a laminar flow bacteria free room.

Oil Phase: The compound No. 18 in example 1-2 was dissolved in tetrahydrofuran and trichloroethylene mixed solution by ultrasound.

Water Phase: Human albumin was dissolved in q.s. 0.1 mol/L hydrochloric acid solution. The mixture was added to the oil phase while stirring vigorously, and stirred vigorously for another 5 min. The mixture was homogenized (600 bar) and cooled by water. The operation was repeated for six times. The organic solvent was removed with a rotary evaporator under low temperature.

The prepared emulsion was sterilized through filtration, injected into xi-lin bottles for freeze-drying in a laminar flow bacteria free room. The emulsion was freeze-dried and sealed using a stopper and aluminum cover.

Example 7-10

| | |
|---|---|
| The compound No. 120 in example 1-2 | 10 mg |
| Medium chain triglyceride | 600 mg |
| Vitamin E polyethylene glycol succinate | 200 mg |
| Lecithin | 100 mg |
| Poloxamer 188 | 200 mg |
| Glycerine | 225 mg |

Process: The following operations were completed in a laminar flow bacteria free room.

Oil Phase: The compound No. 120 in example 1-2 was added to ethanol. Vitamin F polyethylene glycol succinate, medium chain triglyceride and poloxamer 188 were added and heated to dissolve.

Water Phase: 8 ml of 2.25% glycerine solution was added to the oil phase and stirred. Lecithin was added. The mixture was mixed by ultrasound for 10 min. The organic solvent was removed with a rotary evaporator under low temperature.

The prepared emulsion was sterilized through filtration, injected into xi-lin bottles for freeze-drying in a laminar flow bacteria free room. The emulsion was freeze-dried and sealed using a stopper and aluminum cover.

Example 8

Solubility Assay

The structure of compound 129 is quite similar to that of compound 91. The difference between them merely involves the atom at 7-position (shown as the following figure). The solubility assay using them can indicate the change of solubility of 7-azaindirubin relative to indirubin.

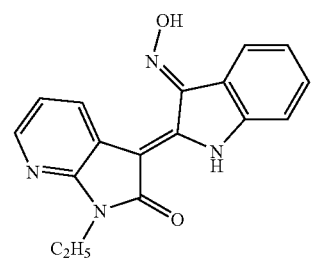

129

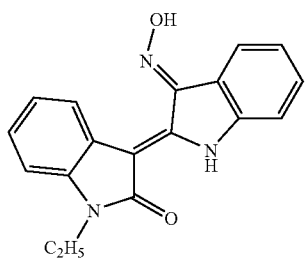

91

Testing Methods: 5 mg of the compound no. 129 and 91 were respectively added into 2 ml solvent at room temperature (20° C.), and stirred to dissolve. The results are shown in table 9.

TABLE 9

Comparison of solubility between compound no. 129 and 91

| Solvents | 129 | 91 |
|---|---|---|
| deionized water | slightly soluble | insoluble |
| methanol | soluble | slightly soluble |
| ethanol | slightly soluble | dissoluble |
| Acetone | slightly soluble | easily soluble |
| trichlormethane | slightly soluble | easily soluble |
| petroleum ether (boiling range: 60~90° C.) | insoluble | slightly soluble |

As shown in the above table, the water solubility of 7-azaindirubin derivatives (129) is increased, while the lipid solubility is decreased. Generally, the water solubility and lipid solubility of indirubin are not good. The lipid solubility of modified indirubin derivatives is increased while the water solubility is decreased, as demonstrated by compound no. 91. The changes in solubility reflect the necessity of studies on 7-azaindirubin derivatives, and will facilitate the absorption of medicine in vivo and the selection of dosage form, etc.

All literatures mentioned in the present application are incorporated by reference herein, as though individually incorporated by reference. Additionally, it should be understood that after reading the description above, many variations and modifications may be made by the skilled in the art, and these equivalents also fall within the scope as defined by the appended claims.

REFERENCES

1. Lundberg A S, Weinberg R A., Control of the cell cycle and apoptosis, Eur J Cancer, 1999, 35: 531-539.
2. Sherr C J. Cancer cell cycles, Science, 1996, 274: 1672-1677.
3. Keyomarsi K., Pardee A B., Redundant cyclin overexpression and gene amplification in breast cancer cells, Proc Natl Acad Sci USA, 1993, 90: 1112-1116.
4. Gray N, Detivand L, Meijer L, et al., ATP-site directed inhibitors of cyclin-dependent kinases, Curr Med Chem, 1999, 6: 859-875.
5. Malumbres M, et al., Targeting cell cycle kinases for cancer therapy, Curr Med Chem, 2007: 14 (9): 969-85.
6. Rudolph J., inhibiting transient protein-protein interactions: lessons from the Cdc25 protein tyrosine phosphatases, Nat. Rev Cancer, 2007, 7 (3): 202-11.
7. Huwe A., Mazitschek R., Giannis A., Small molecules as inhibitors of cyclin-dependent kinases, Angew Chem Int Ed, 2003, 42: 2100-2138.
8. Ji Xiujuan, Wu Kemei, Huang Liang, et. al., Qingdai, Institute of Materia Medica, Chinese Academy of Medical Sciences, Modern Research on Chinese Medicinal Herbs, 1 (1), 1995: 227-257.
9. Nam S., Buettner R, Turkson J., et al., Indirubin derivatives inhibit Stat3 signaling and induce apoptosis in human cancer cells, PNAS, 2005, 102 (17): 5998-6003.
10. Roy K K., Sausville E A. Early development of cyclin dependent kinase modulators, Curr Pharm Design, 2001, 7 (16): 1669-1687.
11. Doklady, Akad Nauk SSSR, 1958, 118: 302-305.
12. Christoph M. S., Pascale H., John M. et al., Synthesis and evaluation of analogues of 10H-indolo[3,2-b]-quinoline as G-quadruplex stabilising ligands and potential inhibitors of the enzyme telomerase, Org. Biomol. Chem., 2004, 2: 981-988.
13. Yao Qizheng, Wang Longgui, Wangzhaohui et. al., CN 1329376C, 2007-8-1.
14. Wang L G, Ossowski L., Ferrari A C., Androgen receptor level controlled by a suppressor complex lost in an androgen-independent prostate cancer cell line, Oncogene, 2004, 23: 5175-5184.
15. Marie K., Marc B., Maryse L., and et al., Independent actions on cyclin-dependent kinases and aryl hydrocarbon receptor mediate the antiproliferative effects of indirubins, Oncogene, 2004, 23: 4400-4412.

The invention claimed is:

1. An azaindole-indole coupled compound represented by the formula (IG) or the pharmaceutically acceptable salts thereof:

Y=Z (IG)

wherein,

Y is an azaindole group represented by formula (Y1) or (Y2);

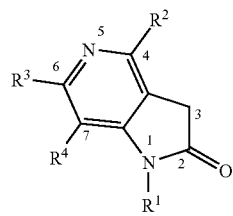

(Y1)

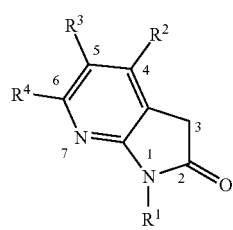

(Y2)

Z is an indole group represented by formula (Z1) or (Z2);

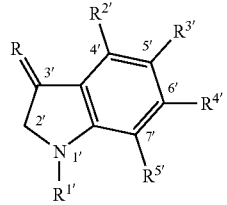
(Z1)

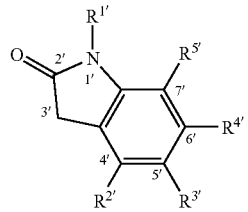
(Z2)

"═" represents a double bond that is located between the 3-position of the azaindole group (Y) and the 2'- or 3'-position of the indole group (Z);

wherein in Y1, Y2, Z1 and Z2, each of $R^1$ and $R^{1'}$ independently represents H or the following groups which may be unsubstituted or substituted by 1 to 3 substituents: $C_1$-$C_6$ alkyl, phenyl, benzyl, acyl, aroyl, glycosyl or diglycosyl protected by acyl, glycosyl or diglycosyl; wherein each of said substituents is selected from: halogen, hydroxyl, $C_1$-$C_3$ alkyl, nitro and amino;

each of $R^3$ and $R^{3'}$ independently represents H, halogen, hydroxyl, or the following groups which may be unsubstituted or substituted by 1 to 3 substituents: $C_1$-$C_4$ alkyl, amino, amido, amide, $C_1$-$C_4$ alkoxy, methylthio, phenyl, phenoxy, aryl, aralkyl, trifluoromethyl, acyl, aroyl, sulfonic group, sulfamoyl, isocyanate, or alkyl isocyanate; wherein each of said substituents is selected from: halogen, hydroxyl, $C_1$-$C_3$ alkyl having, nitro and amino;

each of $R^2$, $R^{2'}$, $R^4$, $R^{4'}$ and $R^{5'}$ is hydrogen; and

R represents oxygen, sulfur, an $NR^6$ group, or an $NOR^6$ group, wherein $R^6$ is H or methyl.

2. The compound of claim 1 or the pharmaceutically acceptable salts thereof, wherein said compounds are represented by formula (I), (II), (III) or (IV), wherein (I) represents 5-azaindirubin compounds, (II) represents 5-azaisoindigo compounds, (III) represents 7-azaindirubin compounds, and (IV) represents 7-azaisoindigo compounds:

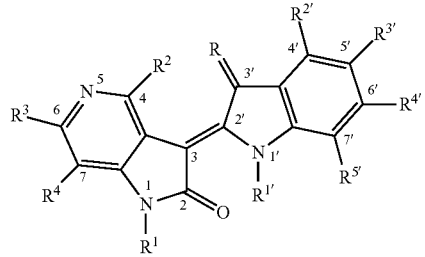
(I)

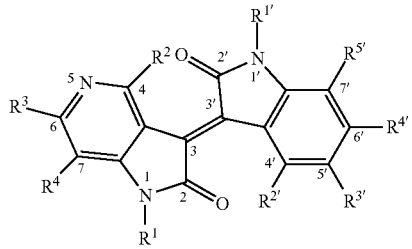
(II)

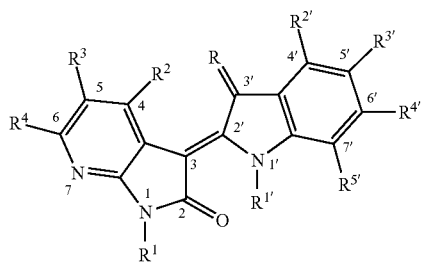
(III)

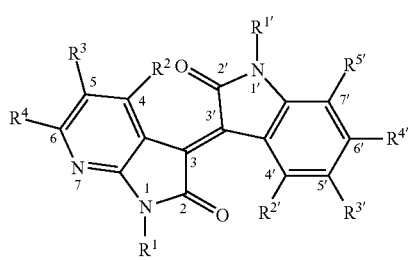
(IV)

wherein, R, $R^1$, $R^2$, $R^3$, $R^4$, R $R^{1'}$, $R^{2'}$, $R^{3'}$, $R^{4'}$ and $R^{5'}$ are defined as in claim 1.

3. The compound of claim 1 or the pharmaceutically acceptable salts thereof, wherein each of $R^1$ and $R^{1'}$ independently represents H, $C_1$-$C_6$ alkyl, phenyl, benzyl, acyl, aroyl, glycosyl protected by acyl, or glycosyl;

each of $R^3$ and $R^{3'}$ independently represents H, halogen, hydroxyl, sulfhydryl, $C_1$-$C_4$ alkyl, amino, amido, amide, $C_1$-$C_4$ alkoxy, methylthio, phenyl, phenoxy, aryl, aralkyl, trifluoromethyl, acyl, aroyl, sulfonic group, or isocyanate;

wherein glycosyl is arabinose, xylose, ribose, mannose, or glucose;

R represents oxygen, sulfur, an $NR^6$ group or an $NOR^6$ group, wherein $R^6$ is H or methyl.

4. The compound of claim 1 or the pharmaceutically acceptable salts thereof, wherein said compound is selected from 5-azaindirubin compounds having a formula I where Y1=Z1 (Table 1: compound Nos 1-59), 5-azaisoindigo compounds having a formula II where Y1=Z2 (Table 2: compound Nos 60-89), 7-azaindirubin compounds having a formula III where Y2=Z1 (Table 3: compound Nos 92-150), and 7-azaisoindigo compounds having a formula IV where Y2=Z2 (Table 4: compound Nos 151-180):

TABLE 1

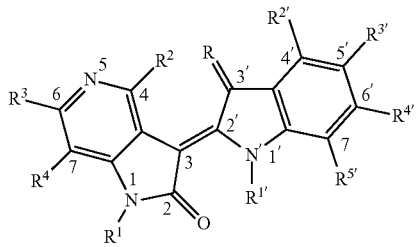

5-azaindirubin compounds having the formula I

| Compound Nos | R¹ | R³' | R |
|---|---|---|---|
| 1 | H | H | O |
| 2 | CH₃ | H | O |
| 3 | CH₃ | OH | O |
| 4 | CH₃ | OCH₃ | O |
| 5 | CH₃ | SCH₃ | O |
| 6 | C₂H₅ | H | O |
| 7 | i-C₃H₇ | H | O |
| 8 | n-C₄H₉ | H | O |
| 9 | CH₂—Ph | H | O |
| 10 | CH₃ | Br | O |
| 11 | CH₃ | Cl | O |
| 12 | C₂H₅ | Br | O |
| 13 | C₂H₅ | Cl | O |
| 14 | i-C₃H₇ | Br | O |
| 15 | i-C₃H₇ | Cl | O |
| 16 | n-C₄H₉ | Br | O |
| 17 | n-C₄H₉ | Cl | O |
| 18 | CH₂—Ph | Br | O |
| 19 | CH₂—Ph | Cl | O |
| 20 | CH₂—Ph | F | O |
| 21 | triacetylribosyl | H | O |
| 22 | PhCO | OCH₃ | S |
| 23 | CH₃CH₂CO | OCH₃ | S |
| 24 | CH₃ | Br | N—OH |
| 25 | CH₃ | Cl | N—OH |
| 26 | CH₃ | Ph | N—OH |
| 27 | CH₃ | SCH₃ | N—OH |
| 28 | C₂H₅ | Br | N—OH |
| 29 | C₂H₅ | Cl | N—OH |
| 30 | i-C₃H₇ | Br | N—OH |
| 31 | i-C₃H₇ | Cl | N—OH |
| 32 | n-C₄H₉ | Br | N—OH |
| 33 | n-C₄H₉ | Cl | N—OH |
| 34 | CH₂—Ph | Br | N—OH |
| 35 | CH₂—Ph | Cl | N—OH |
| 36 | CH₂—Ph | F | N—OH |
| 37 | CH₃ | H | N—OH |
| 38 | C₂H₅ | H | N—OH |
| 39 | i-C₃H₇ | H | N—OH |
| 40 | n-C₄H₉ | H | N—OH |
| 41 | CH₂—Ph | H | N—OH |
| 42 | ribosyl | H | N—OH |
| 43 | glucosyl | H | N—OH |
| 44 | CH₃ | H | N—OCH₃ |
| 45 | CH₃ | Br | N—OCH₃ |
| 46 | CH₃ | Cl | N—OCH₃ |
| 47 | C₂H₅ | H | N—OCH₃ |
| 48 | C₂H₅ | Br | N—OCH₃ |
| 49 | C₂H₅ | Cl | N—OCH₃ |
| 50 | i-C₃H₇ | H | N—OCH₃ |
| 51 | i-C₃H₇ | Br | N—OCH₃ |
| 52 | i-C₃H₇ | Cl | N—OCH₃ |
| 53 | n-C₄H₉ | H | N—OCH₃ |
| 54 | n-C₄H₉ | Br | N—OCH₃ |
| 55 | n-C₄H₉ | Cl | N—OCH₃ |
| 56 | CH₂—Ph | H | N—OCH₃ |
| 57 | CH₂—Ph | F | N—OCH₃ |
| 58 | CH₂—Ph | Br | N—OCH₃ |
| 59 | CH₂—Ph | Cl | N—OCH₃ | wherein each of $R^2$, $R^4$, $R^{1'}$, $R^{2'}$, $R^{4'}$ and $R^{5'}$ represents H in each of compound Nos 1-59 in Table 1;

TABLE 2

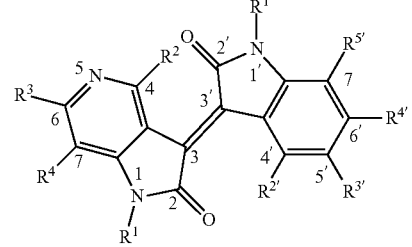

5-azaisoindigo compounds having the formula II

| Compound Nos | R¹ | R¹' | R³' |
|---|---|---|---|
| 60 | CH₃ | H | H |
| 61 | CH₃ | H | Br |
| 62 | CH₃ | H | Cl |
| 63 | CH₃ | H | F |
| 64 | CH₃ | CH₃ | OH |
| 65 | CH₃CH₂CO | H | OCH₃ |
| 66 | PhCO | H | OCH₃ |
| 67 | triacetylribosyl | H | H |
| 68 | C₂H₅ | H | H |
| 69 | C₂H₅ | C₂H₅ | Br |
| 70 | C₂H₅ | H | Cl |
| 71 | C₂H₅ | H | F |
| 72 | C₂H₅ | C₂H₅ | OH |
| 73 | i-C₃H₇ | H | H |
| 74 | i-C₃H₇ | H | Br |
| 75 | i-C₃H₇ | H | Cl |
| 76 | i-C₃H₇ | H | F |
| 77 | i-C₃H₇ | i-C₃H₇ | OH |
| 78 | n-C₄H₉ | H | H |
| 79 | n-C₄H₉ | H | Br |
| 80 | n-C₄H₉ | H | Cl |
| 81 | n-C₄H₉ | n-C₄H₉ | OH |
| 82 | n-C₄H₉ | H | F |
| 83 | n-C₄H₉ | n-C₄H₉ | OCH₃ |
| 84 | CH₂—Ph | H | H |
| 85 | CH₂—Ph | H | Br |
| 86 | CH₂—Ph | CH₂—Ph | Cl |
| 87 | CH₂—Ph | H | F |
| 88 | CH₂—Ph | CH₂—Ph | OH |
| 89 | ribosyl | H | H | wherein each of $R^2$, $R^4$, $R^{2'}$, $R^{4'}$ and $R^{5'}$ represents H in each of compound Nos 60-89 in Table 2;

TABLE 3

7-azaindirubin compounds having the formula III

| Compound Nos | R¹ | R³ | R³' | R |
|---|---|---|---|---|
| 92 | H | H | H | O |
| 93 | CH₃ | H | H | O |

TABLE 3-continued

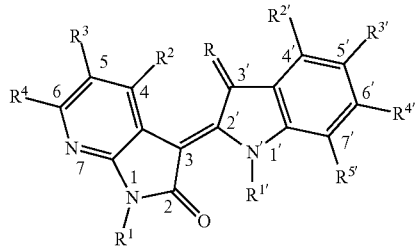

7-azaindirubin compounds having the formula III

| Compound Nos | $R^1$ | $R^3$ | $R^{3'}$ | R |
|---|---|---|---|---|
| 94 | $CH_3$ | $CH_3$ | OH | O |
| 95 | $CH_3$ | $CH_3$ | $OCH_3$ | O |
| 96 | $CH_3$ | $CH_3$ | $SCH_3$ | O |
| 97 | $C_2H_5$ | H | H | O |
| 98 | $i-C_3H_7$ | H | H | O |
| 99 | $n-C_4H_9$ | H | H | O |
| 100 | $CH_2$—Ph | H | H | O |
| 101 | $CH_3$ | H | Br | O |
| 102 | $CH_3$ | H | Cl | O |
| 103 | $C_2H_5$ | H | Br | O |
| 104 | $C_2H_5$ | H | Cl | O |
| 105 | $i-C_3H_7$ | H | Br | O |
| 106 | $i-C_3H_7$ | H | Cl | O |
| 107 | $n-C_4H_9$ | H | Br | O |
| 108 | $n-C_4H_9$ | H | Cl | O |
| 109 | $CH_2$—Ph | H | Br | O |
| 110 | $CH_2$—Ph | H | Cl | O |
| 111 | $CH_2$—Ph | $NHCH_3$ | F | O |
| 112 | triacetylribosyl | $CH_3$ | H | O |
| 113 | PhCO | $CH_3$ | $OCH_3$ | S |
| 114 | $CH_3CH_2CO$ | F | $OCH_3$ | S |
| 115 | $CH_3$ | H | Br | N—OH |
| 116 | $CH_3$ | H | Cl | N—OH |
| 117 | $CH_3$ | $CF_3$ | Ph | N—OH |
| 118 | $CH_3$ | $CH_3$ | $SCH_3$ | N—OH |
| 119 | $C_2H_5$ | H | Br | N—OH |
| 120 | $C_2H_5$ | H | Cl | N—OH |
| 121 | $i-C_3H_7$ | H | Br | N—OH |
| 122 | $i-C_3H_7$ | H | Cl | N—OH |
| 123 | $n-C_4H_9$ | H | Br | N—OH |
| 124 | $n-C_4H_9$ | H | Cl | N—OH |
| 125 | $CH_2$—Ph | H | Br | N—OH |
| 126 | $CH_2$—Ph | H | Cl | N—OH |
| 127 | $CH_2$—Ph | H | F | N—OH |
| 128 | $CH_3$ | H | H | N—OH |
| 129 | $C_2H_5$ | H | H | N—OH |
| 130 | $i-C_3H_7$ | H | H | N—OH |
| 131 | $n-C_4H_9$ | H | H | N—OH |
| 132 | $CH_2$—Ph | H | H | N—OH |
| 133 | ribosyl | $CH_3$ | H | N—OH |
| 134 | glucosyl | $CH_3$ | H | N—OH |
| 135 | $CH_3$ | H | H | N—$OCH_3$ |
| 136 | $CH_3$ | H | Br | N—$OCH_3$ |
| 137 | $CH_3$ | H | Cl | N—$OCH_3$ |
| 138 | $C_2H_5$ | H | H | N—$OCH_3$ |
| 139 | $C_2H_5$ | H | Br | N—$OCH_3$ |
| 140 | $C_2H_5$ | H | Cl | N—$OCH_3$ |
| 141 | $i-C_3H_7$ | H | H | N—$OCH_3$ |
| 142 | $i-C_3H_7$ | H | Br | N—$OCH_3$ |
| 143 | $i-C_3H_7$ | H | Cl | N—$OCH_3$ |
| 144 | $n-C_4H_9$ | H | H | N—$OCH_3$ |
| 145 | $n-C_4H_9$ | H | Br | N—$OCH_3$ |
| 146 | $n-C_4H_9$ | H | Cl | N—$OCH_3$ |
| 147 | $CH_2$—Ph | H | H | N—$OCH_3$ |
| 148 | $CH_2$—Ph | H | F | N—$OCH_3$ |
| 149 | $CH_2$—Ph | H | Br | N—$OCH_3$ |
| 150 | $CH_2$—Ph | H | Cl | N—$OCH_3$ | wherein each of $R^2$, $R^4$, $R^{1'}$, $R^{2'}$, $R^{4'}$ and $R^{5'}$ represents H in each of the compound Nos 92-150 in Table 3;

TABLE 4

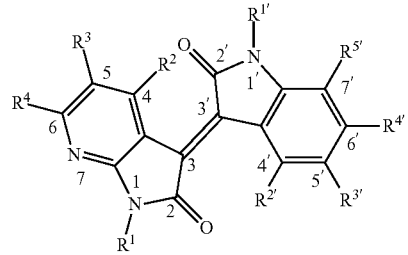

7-azaisoindigo compounds having the formula IV

| Compound Nos | $R^1$ | $R^{1'}$ | $R^3$ | $R^{3'}$ |
|---|---|---|---|---|
| 151 | $CH_3$ | H | H | H |
| 152 | $CH_3$ | H | H | Br |
| 153 | $CH_3$ | H | H | Cl |
| 154 | $CH_3$ | H | H | F |
| 155 | $CH_3$ | $CH_3$ | $CH_3$ | OH |
| 156 | $CH_3CH_2CO$ | H | F | $OCH_3$ |
| 157 | PhCO | H | $CH_3$ | $OCH_3$ |
| 158 | triacetylribosyl | H | $CH_3$ | H |
| 159 | $C_2H_5$ | H | H | H |
| 160 | $C_2H_5$ | $C_2H_5$ | H | Br |
| 161 | $C_2H_5$ | H | H | Cl |
| 162 | $C_2H_5$ | H | H | F |
| 163 | $C_2H_5$ | $C_2H_5$ | $CF_3$ | OH |
| 164 | $i-C_3H_7$ | H | H | H |
| 165 | $i-C_3H_7$ | H | H | Br |
| 166 | $i-C_3H_7$ | H | H | Cl |
| 167 | $i-C_3H_7$ | H | $OCH_3$ | F |
| 168 | $i-C_3H_7$ | $i-C_3H_7$ | H | OH |
| 169 | $n-C_4H_9$ | H | H | H |
| 170 | $n-C_4H_9$ | H | H | Br |
| 171 | $n-C_4H_9$ | H | H | Cl |
| 172 | $n-C_4H_9$ | $n-C_4H_9$ | $SCH_3$ | OH |
| 173 | $n-C_4H_9$ | H | H | F |
| 174 | $n-C_4H_9$ | $n-C_4H_9$ | $OCH_3$ | $OCH_3$ |
| 175 | $CH_2$—Ph | H | H | H |
| 176 | $CH_2$—Ph | H | H | Br |
| 177 | $CH_2$—Ph | $CH_2$—Ph | $SCH_3$ | Cl |
| 178 | $CH_2$—Ph | H | $OCH_3$ | F |
| 179 | $CH_2$—Ph | $CH_2$—Ph | H | OH |
| 180 | ribosyl | H | $CH_3$ | H | wherein each of $R^2$, $R^4$, $R^{2'}$, $R^{4'}$ and $R^{5'}$ represents H in compound Nos 151-180 in Table 4.

5. The compound of claim 1 or the pharmaceutically acceptable salts thereof, wherein said pharmaceutically acceptable salts include salts formed with inorganic acids or organic acids, said inorganic acids include: hydrochloric acid, hydrobromic acid, phosphoric acid, nitric acid, and sulfuric acid; said organic acids include: methanoic acid, acetic acid, propionic acid, succinic acid, naphthalene disulfonic acid (1, 5), asiatic acid, oxalic acid, tartaric acid, lactic acid, salicylic acid, benzoic acid, butylcarboxylic acid, diethylacetic acid, malonic acid, amber acid, fumaric acid, pimelic acid, hexanedioic acid, maleic acid, malic acid, aminosulfonic acid, phenylpropionic acid, gluconic acid, ascorbic acid, nicotinic acid, isonicotinic acid, ethanesulfonic acid, para-toluenesulfonic acid, citric acid and amino acid.

6. A pharmaceutical composition comprising (a) the compound of claim 1 or the pharmaceutically acceptable salts thereof; and (b) pharmaceutically acceptable carriers.

7. The pharmaceutical composition of claim 6, wherein the dosage form of said pharmaceutical composition is low capacity injection, medium capacity injection, high capacity injection, powder injection, emulsion for injection, tablet, pill, capsule, paste, cream, patch, liniment, powder, spray, implantable agent, drop, suppository, ointment; various nano preparations; or liposomes.

8. An azaindole-indole coupled compound represented by the formula (IG) or the pharmaceutically acceptable salts thereof:

Y=Z   (IG)

wherein,

Y is an azaindole group represented by formula (Y1) or (Y2);

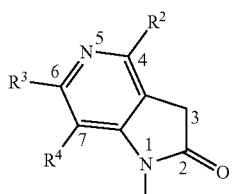
(Y1)

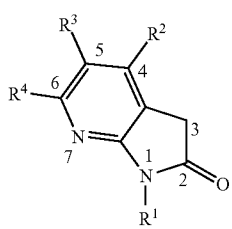
(Y2)

Z is an indole group represented by formula (Z1) or (Z2);

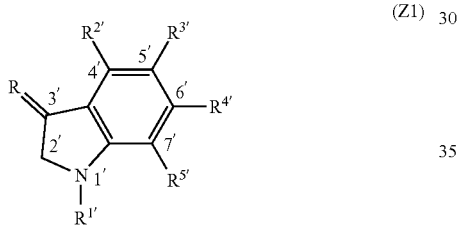
(Z1)

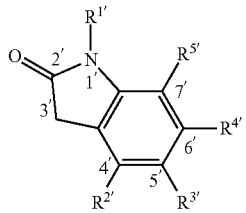
(Z2)

"=" represents a double bond that is located between the 3-position of the azaindole group (Y) and the 2'- or 3'-position of the indole group (Z);

wherein in Y1, Y2, Z1, and Z2, each of $R^1$ and $R^{1'}$ independently represents H or the following groups which may be unsubstituted or substituted by 1 to 3 substituents: $C_1$-$C_6$ alkyl, benzyl, acyl, aroyl, glycosyl or diglycosyl protected by acyl; wherein said substituents are selected from, $C_1$-$C_3$ alkyl;

each of $R^3$ and $R^{3'}$ independently represents H, halogen, hydroxyl, or the following groups which may be unsubstituted or substituted by 1 to 3 substituents: $C_1$-$C_4$ alkyl, amino, $C_1$-$C_4$ alkoxy, methylthio, phenyl, or trifluoromethyl; wherein said substituents are selected from: halogen and $C_1$-$C_3$ alkyl;

each of $R^2$, $R^4$, $R^{2'}$, $R^{4'}$ and $R^{5'}$ is hydrogen; and

R represents oxygen, sulfur, or an $NOR^6$ group, wherein $R^6$ is H or methyl.

* * * * *